United States Patent [19]

Pincus et al.

[11] Patent Number: 5,769,793
[45] Date of Patent: *Jun. 23, 1998

[54] SYSTEM TO DETERMINE A RELATIVE AMOUNT OF PATTERNNESS

[75] Inventors: Steven M. Pincus, 990 Moose Hill Rd., Guilford, Conn. 06437; Robert A. Neidorff, Bedford, N.H.

[73] Assignee: Steven M. Pincus, Guilford, Conn.

[*] Notice: The term of this patent shall not extend beyond the expiration date of Pat. No. 5,191,524.

[21] Appl. No.: 716,059

[22] Filed: Sep. 19, 1996

Related U.S. Application Data

[63] Continuation-in-part of Ser. No. 11,409, Jan. 29, 1993, Pat. No. 5,562,596, which is a continuation-in-part of Ser. No. 404,737, Sep. 8, 1989, Pat. No. 5,191,524.

[51] Int. Cl.$^6$ .................................. A61B 5/0402
[52] U.S. Cl. .................... 600/515; 600/300; 600/544; 600/546; 128/920
[58] Field of Search ....................... 128/920, 696, 128/702, 705, 731, 733, 630; 600/509, 515, 518, 544, 546, 300

[56] References Cited

U.S. PATENT DOCUMENTS

| 4,018,219 | 4/1977 | Hojaiban ........................ 128/2.06 A |
| 4,680,708 | 7/1987 | Ambos et al. .................... 364/417 |
| 4,732,157 | 3/1988 | Kaplan et al. ................... 128/696 |
| 4,802,491 | 2/1989 | Cohen et al. .................... 128/702 |
| 4,932,610 | 6/1990 | Maestrello ....................... 244/203 |
| 4,934,374 | 6/1990 | Ostlund et al. ................... 128/695 |
| 4,974,162 | 11/1990 | Siegel et al. .................. 364/413.06 |
| 5,112,292 | 5/1992 | Hwang et al. ..................... 600/16 |
| 5,191,524 | 3/1993 | Pincus et al. ................... 128/696 |
| 5,222,698 | 6/1993 | Nelson et al. .................... 244/203 |
| 5,437,285 | 8/1995 | Verrier et al. ................... 128/702 |
| 5,560,370 | 10/1996 | Verrier et al. .................. 128/705 |

OTHER PUBLICATIONS

Gleick, J., "Chaos: Making a New Science," Viking Penguin Inc., New York, NY, pp. 275–300, (1987).
Eckmann, J.P., et al., "Ergodic Theory of Chaos and Strange Attractors," *Reviews of Modern Physics*, 57(3), (Jul. 1985).
Browne, M.W., "In Heartbeat, Predictability Is Worse Than Chaos," *The New York Times*, (Jan. 1989).
Billingsley, P., "Ergodic Theory and Information," New York: Wiley, 1965: p. 60–94.
Grassberger, P., et al., "Estimation of the Kolmogorov Entropy from a Chaotic Signal," *Physical Review A*, 28(4):2591–2593, (Oct. 1983).
Zbilut, T., et al., "Decreased Heart Rate Variability in Significant Cardiac Events," *Crit. Care Med.*, 16(1):64–66, Abstract Only, (1988).
Inouye, T., et al., "Quantification of EEG Irregularity by use of the Entropy of the Power Spectrum," 79(3):204–210, *Electroencephalogr. Clin. Neurophysiol*, Abstract Only, (1991).

(List continued on next page.)

*Primary Examiner*—William E. Kamm
*Assistant Examiner*—Kennedy J. Schaetzle
*Attorney, Agent, or Firm*—Hamilton, Brook, Smith & Reynolds, P.C.

[57] ABSTRACT

A quantification of approximate entropy is determined on a set of data by comparing subsets of the data. The comparison reveals the regularity and stability of similar patterns amongst subsets of the data. The comparisons perform such that the contribution of noise to measurement of the regularity and stability is minimized. Quantitative values are assigned to measure the degree of regularity and stability. From these quantitative values a single output measure is generated indicative of the amount of patternness of the sequence of data. The calculations required to determine this approximate entropy are preferably performed within a data processing system. Numerous peripheral devices may be attached to such a data processing system. The types of data for which the approximate entropy may be calculated include any sets of data wherein the amount of patternness is sought.

49 Claims, 10 Drawing Sheets

OTHER PUBLICATIONS

Pincus, S.M., et al., "Approximate Entropy: Statistical Properties and Applications," *Commun. Statist.—Theory Meth.*, 21(11):3061–3077, (1992).

Pincus, S.M., "Approximating Markov Chains," *Proc. Natl. Acad. Sci. USA*, 89:4432–4436, (May 1992).

Pincus, S.M., "Approximate Entropy as a Measure of System Complexity," *Proc. Natl. Acad. Sci. USA*, 88:2297–2301, (Mar. 1991).

Parer, W.J., et al., "Validity of Mathematical Methods of Quantitating Fetal Heart Rate Variability," *Am. J. Obstet. Gynecol.*, 153(4):402–409, (Oct. 1995).

Pincus, S.M., et al., "A Regularity Statistic for Medical Data Analysis," *J. Clin. Monit.*, 7(4):335–345, (Oct. 1991).

Kaplan, D.T., et al., "Aging and the Complexity of Cardiovascular Dynamics," *Biophys. J.*, 59:945–949, (Apr. 1991).

Lipsitz, L.A., et al., "Loss of 'Complexity' and Aging," *JAMA*, 267(13):1806–1809, (Apr. 1992).

Pincus, S.M., et al., "Quantification of Hormone Pulsatility Via An Approximate Entropy Algorithm," *Am. J. Physiol.* 262 (Endocrinol. Metab. 25), pp. E741–E754, (1992).

Pincus, S.M., et al., "Approximate Entropy: A Regularity Measure for Fetal Heart Rate Analysis," *Obstet. Gynecol.*, 79(2):249–255, (Feb. 1992).

Fox, R.W., et al., "Introduction to Fluid Mechanics," 2d Ed., John Wiley & Sons: New York 1978, pp. 38–46, 316, 332–333, 354–367, 424–462.

| SLOT | U(1) | U(2) | U(3) | U(4) | U(5) | U(6) | U(7) | U(8) | U(9) |
|---|---|---|---|---|---|---|---|---|---|
| VALUE | 1 | 0 | 1 | 0 | 1 | 0 | 1 | 0 | 1 |
FIG. 2A
| SLOT | U(1) | U(2) | U(3) | U(4) | U(5) | U(6) | U(7) | U(8) | U(9) |
|---|---|---|---|---|---|---|---|---|---|
| VALUE | * | * | 1 | * | * | 0 | * | * | 1 |
* Random where both zero and one occur with probability $\frac{1}{2}$
FIG. 2B
FIG. 4A
FIG. 4B
FIG. 4C

SYSTEM TO DETERMINE A RELATIVE AMOUNT OF PATTERNNESS

RELATED APPLICATIONS

This application is a Continuation-In-Part of U.S. patent Ser. No. 08/011,409 filed Jan. 29, 1993, (now U.S. Pat. No. 5,562,596) which is a Continuation-In-Part of U.S. Pat. Ser. No. 07/404,737 filed. Sep. 8, 1989 (now U.S. Pat. No. 5,191,524), the teachings of which are incorporated herein by reference in their entirety.

BACKGROUND OF THE INVENTION

Diagnosis of many medical conditions requires the collection and analysis of medical data. In interpreting this data, doctors and other medical personnel have generally applied a number of rules of thumb, or qualitative assessments, to reach their diagnosis. These rules of thumb have proven to be quite useful but are not comprehensive, because certain ailments and abnormalities cannot be adequately identified merely by applying currently established rules of thumb.

One example where rules of thumb are applied is in monitoring electrocardiograph (EKG) data. EKG data is typically presented as a graphical output of a patient's heart activity. Doctors look for recognizable abnormalities and particular flags in the EKG data, as warning signals of health problems. They can discern certain abnormalities amongst this data by visually inspecting the graphical output; however, other important, more subtle abnormalities may go undetected. As such, the visual examination of data does not provide a complete diagnostic tool because some potentially significant abnormalities in the data are not apparent from visual inspection.

Another example of where rules of thumb are applied is in monitoring hormone secretion in an attempt to identify abnormal physiology. In the past fifteen years, endocrinologists have determined that episodic hormone secretion is a widespread phenomenon. The discovery of the link between abnormal pulsatility and certain hormonal disorders has prompted the recognition that a greater understanding of hormone secretion patterns, statistic to analyze hormone secretion data, and underlying system models could be of keen importance. To date, a number of pulse-identification algorithms have been developed to analyze hormone level data. These methods have been useful in detecting abnormal secretory patterns in some instances, and the expectation is that refined versions of these algorithms, applied to increasingly accurate and numerous data, will detect further abnormalities in hormonal secretion, earlier in the course of disease.

Another rule of thumb is used in fluid dynamics to design structures. Through experimentation, a force ratio between the inertial force and the viscous force of fluids has been developed. This ratio, or Reynolds number, is correlated with the formation of wakes when a fluid flows past an object. In systems with a fluid flowing at a fixed velocity and impinging on a rigid object, the wake behavior can be modelled. The Reynolds number cannot be easily used to model more complex systems.

For example, the Reynolds number cannot easily model a human heart because blood flow is not constant and the heart is not a rigid structure. The blood changes the heart surface dynamically and nonlinearly. Designers of artificial hearts rely heavily on trial and error, with the testing often being fatal. Artificial heart valves change the pattern of fluid flow in the heart, which creates areas of turbulence and areas of stagnation. Blood clots that form in the stagnation areas often find their way to the patient's brain, causing strokes.

SUMMARY OF THE INVENTION

The present invention concerns the quantification of a relative measure of patternness of a set of data. This data may be medical data or any other data for which it would be useful to know the relative measure of patternness present in the data. In determining the relative measure of patternness, subsets of data are first compared to determine the regularity and stability of similar patterns among the subsets. The detrimental effects of noise in these comparisons are minimized by the imposition of an imbedded algorithm. Intermediate values are then assigned to quantify the regularity and stability of similar patterns among the subsets that are compared. The output measure of patternness is based on the average of these assigned intermediate values. This measure is forwarded as an output signal to its destination.

In a preferred embodiment, the set of data is medical or other data, and the measure of patternness is a new information-theoretic measure called "approximate entropy," or ApEn. Moreover, the contribution of noise below a specified tolerance level to this measure is minimized as noted above.

A particular application for which ApEn may be valuable is in the analysis of electrocardiograph data such as beat-to-beat heart rate data derived from an EKG. When used in such an application, the R—R intervals between consecutive beats are first extracted from EKG data. These R—R intervals are a standard measure of the length of heartbeats. They are then averaged for a given length of time (preferably specified by the user) to produce a set of R—R interval averages. These averages are then analyzed as described above.

Another application for which the application of ApEn may be valuable is in the analysis of hormone secretion behavior, measured typically from blood samples. Pulsatile secretions are found in many hormones, so there is great potential for this measure to identify deviations from normal secretion patterns, and to identify diseases pre-onset of symptoms. The input data for patternness analysis in this case is a series of blood level measurements of a specified hormone.

The present invention may also be used with other types of medical data. For instance, it may be used with electro-encephalograph data, electro-ocolgram data, electromyogram data, and respiratory measurement data. To analyze data via the present invention, it is often necessary to first convert the data into digital form before processing it.

The present invention may also have significant non-medical applications. It may be used to analyze stock market data, such as the Dow Jones index, individual stock prices, and bond prices over time. It may also be used to analyze aerodynamic, hydrodynamic, and astronautic data, such as velocities, momenta, pressure, position data, etc. and especially to provide a figure-of-merit for turbulent behavior of these data. The processing of the data is carried out by a data processing system. The data processing system should include a comparator for performing a comparing step in which contiguous runs of data of a prescribed length are compared to a plurality of other contiguous runs of data of the same length to determine measures of regularity and stability. The measure of stability should also act as a filter to remove noise substantially below a specified tolerance level. The processor aggregates these regularity and stability measures to generate a single number as an approximate entropy value, ApEn.

The approximate entropy value may be forwarded to a number of different output peripheral devices. For instance, the approximate entropy value may be output to an alarm that signals when the approximate entropy value lies outside a safe range. In addition, the approximate entropy value may be employed with a meter that displays the approximate entropy value, as well as with an automated adjustor that automatically reacts in response to the approximate entropy value. The response performed by the adjustor includes adjusting an external stimulus by dispensing medication, performing medical procedure, or disrupting a flow stream. Further, a storage device may be attached to the data processing system to record the approximate entropy value over a period of time.

The system may be used to control the flow of a medium across or through a region constrained by a primary solid. The primary solid partially interferes with the flow of the medium. The system comprises at least one sensor, a processor, a compensated negative feedback control, an actuator, and a secondary solid. The sensor is located in proximity to the primary solid to measure and quantify a flow parameter of the medium. The processor is coupled to the sensor to determine a time-varying measure of relative patternness for the medium in proximity to the primary solid. In particular, the measure of relative patternness is quantified by approximate entropy. The negative feedback control is coupled to the processor and generates a time-varying control signal in response to the time-varying measure of relative patternness. An actuator is coupled to the negative feedback control to produce a driving force in response to the control signal. The actuator urges a secondary solid to affect the flow characteristics of the medium in proximity to the primary solid.

In particular, a flow control system is used to control fluid flow to optimize turbulence in the medium. The sensor measures flow parameters such as speed, pressure, and direction of flow. In response, the actuator urges motion in the secondary solid, such as a constrictor, flap, or vibrating plate. The secondary solid interferes with the wake caused by the primary solid.

Furthermore, the system can be used to assess deoxyribonucleic acid (DNA) sequences. A DNA sequence from an automated DNA sequencer can be evaluated using an ApEn computer. Such a system can automatically detect altered genes and evaluate the accuracy of DNA sequences. For example, a DNA sequencer embodying the invention can automatically read sequencing gels and produce an accurate DNA sequence listing.

BRIEF DESCRIPTION OF THE DRAWINGS

FIGS. 2A–B show sample sets of data.

FIGS. 4A–C show three different sample sets of data.

DETAILED DESCRIPTION OF PREFERRED EMBODIMENTS OF THE INVENTION

A preferred embodiment of the present invention concerns the determination of a relative measure of patternness in sets of data, especially sets of medical data. In particular, a data processing system 2 is utilized to produce a single number measuring the relative measure of patternness in a set of medical data, such as electrocardiograph (EKG) or hormone secretion data. This single number constitutes a measure of regularity or "complexity," which is an approximate entropy value in the data derived from the set of medical data, and will be referred to hereinafter as approximate entropy or ApEn. It is useful in determining, from the set of medical data, both the well-being of the data producing organ, or other part of the body, and the general well-being of the individual. It is also useful in other applications that will be discussed below.

Figure 1:
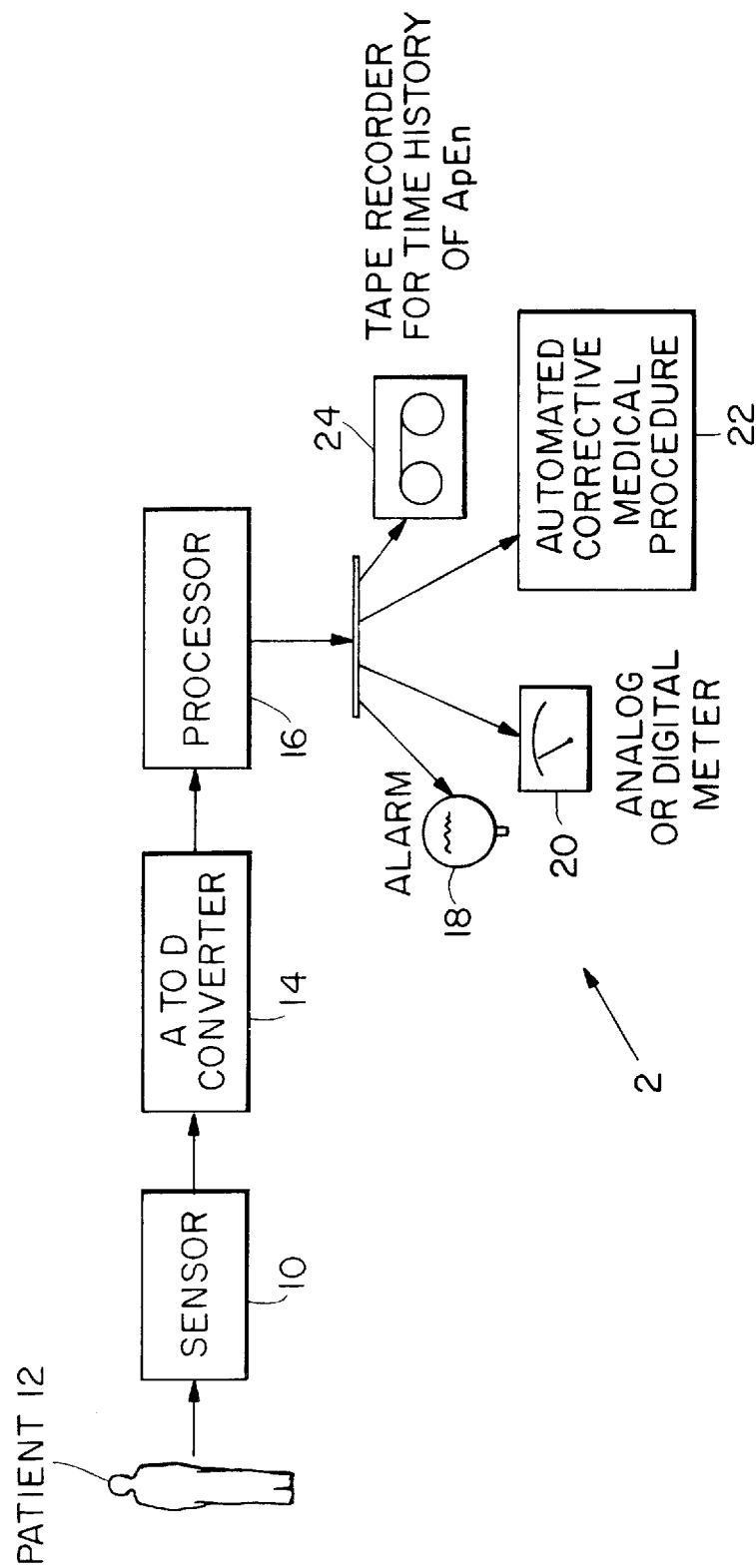
FIG. 1 shows a data processing system that calculates an approximate entropy value and acts on the calculated value.

FIG. 1 shows the major components of the data processing system used to obtain this approximate entropy value. Specifically, a sensor 10 is applied to a patient 12 to obtain medical data. Techniques for applying such a sensor 10 are well known in the prior art. Once the sensor 10 is appropriately attached to the patient 12, the sensor begins receiving data relating to the patient's system. This data is typically received in analog form and may be output as a graph, known as a tracing.

Although the analog medical data is useful as a graphical representation of the data, it is difficult to process. Hence, the present system includes an analog to digital converter 14 that samples the analog waveform of the medical data tracing to produce a digital representation of the samples. This digital representation is then forwarded to a processing means 16 wherein the digital data is processed to produce the approximate entropy measure.

The system extracts data intervals from the set of medical data and averages them for a given, user-specified short length of time to produce an average set of data intervals. This average set of data intervals is processed to obtain the approximate entropy measure. The user can choose to work with the data intervals directly too. The processing means 16 contains the appropriate software to perform the necessary calculations to obtain the approximate entropy measure. This software can be written in any of a variety of high level languages such as Fortran, C, Pascal, etc. The details of the software will be discussed more below.

The resulting approximate entropy measure as computed by the processing means 16 can be output to a number of different types of peripheral devices. For instance, the approximate entropy measure can be forwarded to an alarm 18 which indicates when the measure lies outside an acceptable range. Further, the approximate entropy measure can be forwarded to an analog or digital meter 20 that shows the current value of the measure as computed by the processing means. Still further, the approximate entropy measure can be sent to an automated corrective medical procedure device 22. Such a device 22 automatically reacts to remedy a difficulty noted by an unsatisfactory approximate entropy measure. For example, if the approximate entropy measure indicates a low level of a vital hormone, the automated corrective procedure device 22 can excrete a given quantity of the hormone in response to the low approximate entropy measure.

Another alternative is for the approximate entropy measure to be recorded on a tape recording or other recording means 24 such that a time history of the approximate entropy measure is kept. Each of these peripherals 18, 20, 20, 22 and 24 need not exist in isolation. The system can be configured such that all of these devices are connected simultaneously to the processing means 16. Moreover, peripheral devices other than those described can be attached to the processing system. These suggested devices are not meant to be exhaustive of the personal devices that lie within the scope of the present invention.

Such a measure of patternness of a set of time-series data is especially useful in medical applications. Medical personnel have for years visually examined hard copies of medical data presented in graphical form to attempt to discern abnormalities in the data. Such efforts, however, can only discern patternness at a superficial level that lacks the usefulness and completeness of the measure of the present invention. Moreover, past efforts have not been able to distill the patternness into a single comprehensive measure that is both readily usable and robust to noise.

The present invention can be used with medical data such as electrocardiograph (EKG) data, electroencephalogram (EEG) data, electrooculogram (EOG) data, electromyogram (EMG) data, and respiratory data such as ventilation pulses that measure tidal volume. It can also be used to analyze the patternness and pulse stability exhibited in hormone secretion. Further, it can be used to analyze non-medical data, such as stock market data over time; and aerodynamic, hydrodynamic, and astronautic data, to provide a figure-of-merit for turbulent behavior of these data. This list is not intended to be exhaustive of the potential applications of the present invention; rather it is merely intended to be illustrative. The present invention can, in fact, be useful anytime wherein knowing a relative measure of patternness in a set of data is useful.

The historic development of mathematics to quantify regularity has centered around various types of entropy measures. Entropy, in a different context, has been an integral part of the modern quantitative development of thermodynamics, statistical mechanics, and information theory. Although, intuitively, the entropy quantifications in physics address the issues of randomness and regularity, the equations themselves involve integrals and derivatives of known functions, such as work, temperature, and energy (Feynman, R. P., *The Feynman Lectures on Physics,* Vol. 1, Reading:Addison-Wesley, 1963: 44.10–44.13). In modern probability theory, entropy is explicitly defined, given a probability distribution (measure) for elements of a set (Billingsley, P., *Ergodic theory and information,* New York:Wiley, 1965: 60–94). This definition coincides with intuition in that systems having more random probability distributions have greater entropy. Nonetheless, these approaches to entropy definition are not directly applicable to time-series data analysis.

Kolmogorov-Sinai (K-S) entropy (Eckmann, J. P., and D. Ruelle, "Ergodic Theory of Chaos and Strange Attractors," *Rev. Mod. Phys.* 57(3) (July 1985): 617–656) generalizes the probabilist's definition of entropy, in a theoretical setting, and paves the way to entropy equations for time-series data, as discussed below. There has been particularly keen interest in the development of these equations in the last 10 years, since entropy has been shown to be a critical "summary" statistic in nonlinear dynamical system analysis and chaos (Crutchfield, J. P., and N. H. Packard, "Symbolic Dynamics of One-Dimensional Maps: Entropies, Finite Precursor, and Noise," *Int. J. Theor. Phys.* 21 (1982): 433–465). In 1983, Grassberger and Procaccia developed an equation, based on the K-S entropy, to measure the entropy of a time series (Grassberger, P., and I. Procaccia, "Estimation of the Kolmogorov Entropy From a Chaotic Signal," *Phys. Rev. A* 28 (1983): 2591–2593); this equation, and a slight variation produced by Takens (Takens, F., "Invariants Related to Dimension and Entropy," in Atas do 13, Rio de Janeiro: Col. Brasiliero de Matematicas, 1983), have become the "standard" entropy and regularity measures for use with time-series data.

The method for ApEn is somewhat similar in appearance to two algorithms that estimate the Kolmogorov-Sinai entropy, given by Eckmann and Grassberger. Approximate entropy has three technical advantages in comparison to Kolmogorov-Sinai entropy for general statistical usage. Kolmogorov-Sinai entropy is badly compromised by tiny amounts of noise, generally requires a vast amount of input data to achieve convergence, and is usually infinite for random processes. Approximate entropy is nearly unaffected by noise of magnitude below "r," gives meaningful information with 1000 points, and is finite for both random and deterministic processes. This last item allows ApEn to distinguish versions of random processes, reasonable candidates for general medical processes including heart rate models, from each other, whereas Kolmogorov-Sinai entropy would be unable to do so.

ApEn provides a widely applicable equation for the data analyst that will distinguish data sets by a measure of regularity. The intuition motivating ApEn is that if joint probability measures for reconstructed dynamics that describe each of two systems are different, than their marginal distributions on a fixed partition are likely different. In contrast, the K-S entropy was developed by Kolmogorov to resolve the theoretical mathematical question of whether two Bernoulli shifts are isomorphic, and is primarily applied by ergodic theorists to well-defined transformations, with no noise and an infinite amount of "data" available.

There are several indication that the approximate entropy measure may detect a broad range of problems in the human body heretofore undetected. It has recently become known that much of the human body exhibits possibly chaotic, and random behavior when functioning properly. As noted in James Gleick, *Chaos: Making a New Science* (New York-:Penquin Books, 1987: 275–300) (summarizing numerous primary sources), a change in the nature of this normally irregular behavior may be a signal that problems exist. Unfortunately, the changes in this irregular behavior usually are not readily discernible by visual review of the data that measure the body's function (EKG, EEG, etc.). Approximate entropy provides a measure for discerning (subtle) changes in the degree of the irregular behavior exhibited, and hence in identifying improper body function.

The ability of approximate entropy to directly measure feedback system change in many systems may allow this measure to predict ailments in the human body pre-onset. Many systems of the human body exhibit coupled, or feedback behavior when functioning properly. For example, the male reproductive system can be viewed as a feedback loop. Specifically, the hormone LHRH determines LH production, which determines testosterone production, and the testosterone production, in turn, determines LHRH production. The heart, consisting of the sinoatrial node and the atrioventricular junction, is another example of such a coupled feedback mechanism. Changes in this feedback loop, either in extent or in nature, may cause or indicate disease.

Changes in feedback are often reflected in corresponding changes in the regularity of systems. Decoupling and lessening feedback is explicitly noted by decreasing approximate entropy in the system. This barometric property of entropy may have two important medical implications. First, it may allow for the identification of insidious diseases not otherwise detectable, pre-onset of symptoms, and second, it may help to identify the physiologic system change that is the cause of some diseases.

The approximate entropy measure is somewhat similar in appearance to an algorithm provided by Eckmann et al. for the Kolmogorov-Sinai (K-S) entropy which can be expressed mathematically as:

$$\text{Entropy} = \lim_{r \to 0} \lim_{m \to \infty} \lim_{n \to \infty} [\phi^m(r) - \phi^{m+1}(r)] \qquad (1)$$

Equation 1 is disclosed in Eckmann, with Φ as given therein. Unfortunately, Equation 1 has little general practical utility, for two reasons. First, accurate entropy calculations for most data sets cannot be performed in "finite" time; that is less than multiple of years of computer time per calculation. Part of the difficulty in calculating K-S entropy lies in that it is a triple-limit and that the computational time to ensure accuracy grows exponentially with m. Second, Equation 1 degrades badly (disintegrates) when noise is present because the presence of noise in the data causes the entropy calculation to explode to very high values. With Kolmogorov-Sinai, entropy noise considerations dominate other system characteristics. Therefore, it has proven to be a measure that lacks robustness. The present invention, in contrast, overcomes these difficulties, and provides a relative measure of patternness that is both readily calculated for any time-series data and robust to noise.

The basic approach of the method of the present invention is to compare contiguous runs of the data, so as to look for patterns amongst the subsets. All groups of contiguous subsets of the data are compared against each other, in search of the proportion of similar patterns for each "template" pattern. The approximate entropy measure is derived from an average of these proportions.

A step-by-step computation of approximate entropy will next be explained for the preferred embodiment. The computation is performed for the example series of data given in FIG. 2A, a "perfectly patterned" series of alternating 0's and 1's. A more mathematically formal description of the preferred embodiment follows.

FIG. 2A shows an example series of data that is useful in explaining the mechanics of calculating the approximate entropy measure. In this preferred embodiment, the processing means 16 receives such a series of data and begins processing it. Two system parameters are set before the processing means 16 calculates the approximate entropy measure. These parameters can be either encoded in the software or requested from the user of the system. These parameters include a value r, which stands for radius, and is a filter factor, and a value m which is the length of a run or template pattern length. Defining these variables as fixed is quite different from what is done with K-S entropy, for K-S entropy is calculated as a limiting value as these variables approach zero and infinity, respectively. Moreover, the number of elements in the set of data is fixed in the present invention. K-S entropy, on the other hand, requires that the number of elements approaches infinity. The significance of these parameters will be discussed in more detail below. It is the fixing of the two parameters, m and r, that provides the general practical utility of the preferred embodiment of approximate entropy.

Figure 3:
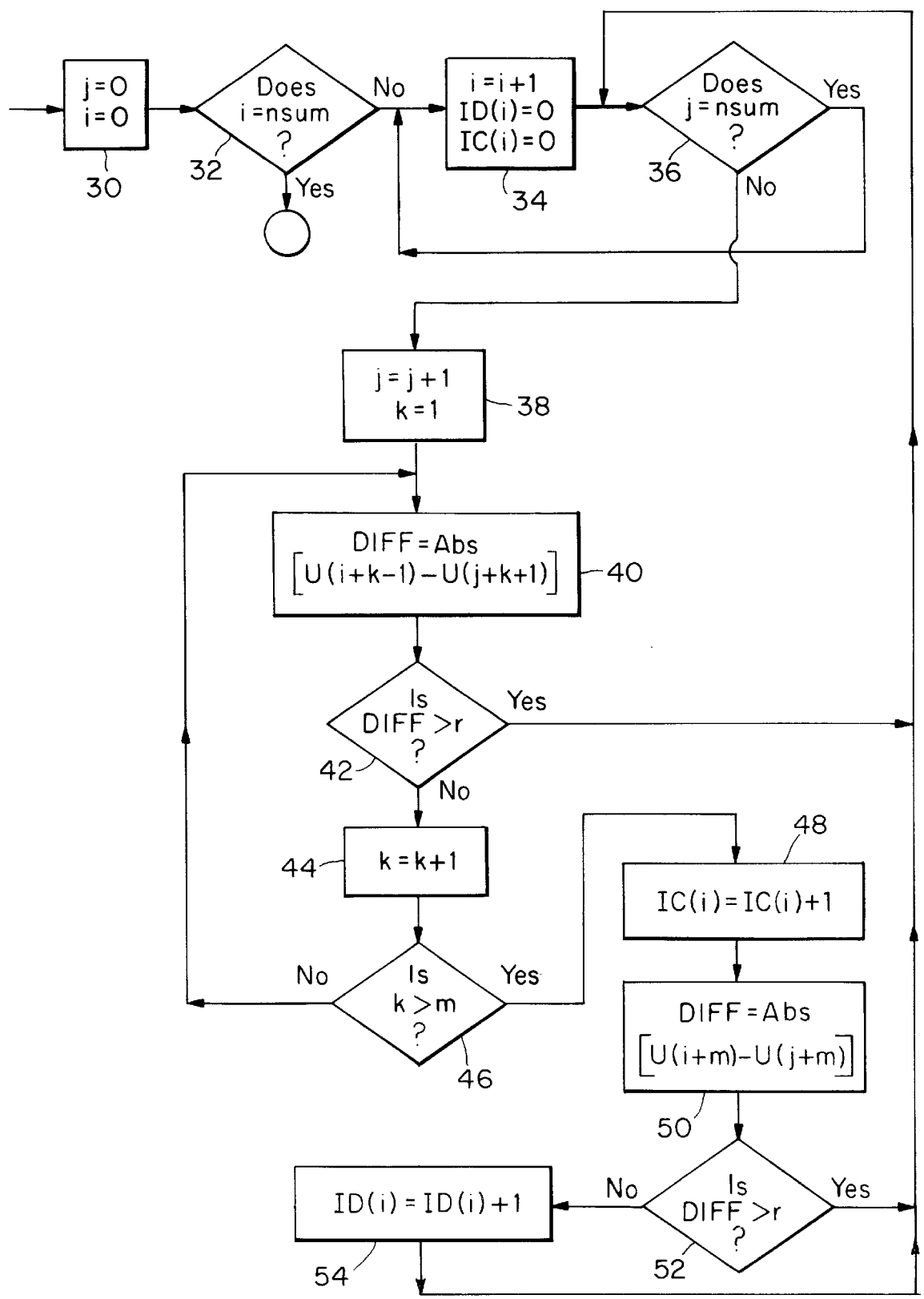
FIG. 3 shows a flow chart of how the approximate entropy measure is calculated.

Having set these parameters, the present invention proceeds to perform the necessary calculations to compute the approximate entropy measure. The processing means 16 begins by following the steps illustrated in FIG. 3. The numerical data are given as U(1), U(2), . . . , U(nsum). The steps performed by the processing means 16 are performed primarily within a loop where the index of the loop, i, goes from one to the number of elements in the set of data (denoted as nsum) as indicated by steps 30, 32 and 34. At the beginning of this loop, the first locations in two memory arrays are set at a value of zero (the two memory arrays ID(i) and IC(i)). Nested within the larger loop is a smaller loop that has a loop index, j, that also goes from 1 to nsum (steps 30, 36 and 38).

The main part of this method involves calculations to appropriately fill the arrays ID(i) and IC(i), for i=1, 2, . . . , nsum. The final calculation of the approximate entropy follows in a straightforward manner from all these ID and IC values, as discussed below.

Within the inner loop, the variable k is set initially at a value of 1 (step 38). To keep track of the locations of comparisons k is used within this inner loop as a counter. Next, the value of the variable DIFF is calculated as the absolute value of the difference U(i+k−1)−U(j+k−1) (step 40). The variable DIFF is equal to the absolute value of the difference between the elements within the sets of data that are currently being compared. Once DIFF is calculated, the system checks to see whether DIFF is greater than r (step 42). The system, in other words, checks to see whether U(i+k−1) lies within a distance less than the radius (tolerance level) from U(j+k−1). If DIFF exceeds the radius, j is incremented (step 38). However, if the difference is less than or equal to the radius, k is incremented (step 44). In the event that k is incremented, the system checks to see whether k is greater than m (step 46). This comparison is to check whether the value being examined lies within or outside the run (or window) length currently being compared as designated by m. If k is not greater than m, then DIFF is recalculated using the new value of k (i.e. step 40 is repeated with the new k). The new value of k shifts the comparison over by one element. For instance, if U(1) and U(2) had been initially compared after k was incremented, DIFF is recalculated between U(2) and U(3).

Suppose, in contrast, that k is greater than m (step 46). In that case, the array location at IC(i) is incremented by 1 (step 48). Furthermore, DIFF is recalculated to equal the absolute value of U(i+m)−Uj+m) (step 50). This calculation is to determine whether the corresponding elements located a run length away from the elements that were just compared are also close enough for their difference to lie within the radius. Step 52 checks to see whether this difference lies within the radius. If the difference is not greater than the radius, the array location ID(i) is incremented by 1 (step 54). If the difference is greater than the radius, only the value of j is incremented by 1. The steps are repeated until both i and j equal nsum.

For illustrative purposes, suppose that the system processes the data shown in FIG. 2A. Further suppose that m=2 and r=0.5. In the first iteration of the steps shown in FIG. 3, i=1 and j=1. Hence, the difference is calculated as the difference between U(1) and U(1) (step 40). This difference is zero which means that the difference is less than the radius 0.5 (as checked by step 42). As such, k is incremented by 1 (step 44). However, k, is not greater than m (i.e. 2) (step 46); thus, DIFF is recalculated (step 40). This subsequently evaluated value of DIFF is derived by comparing U(2) and U(2). In making that comparison, DIFF is again 0 (step 42). After incrementing k (step 44), k is greater than m (step 46), so IC(1) is incremented (step 48) from 0 to 1. Then DIFF is recalculated (step 50) between U(3) and U(3), and because DIFF=U(3)−U(3)=0, ID(1) is incremented by 1, from 0 to 1 (step 54).

Once ID(1) has been incremented, the value of j is also incremented (step 38) to j=2. The result is that DIFF is next calculated between U(1) and U(2) (step 40). Because the absolute value of DIFF is greater than the radius (1 is greater than 0.5), the value of j is incremented once again.

With j having a value of 3 and i having a value of 1, the system sets the value k at 1 (step 38), and it then computes the absolute value of the difference between U(1) and U(3) (step 42). Because both U(1) and U(3) are equal to 1, the difference between them equals zero. The difference lies within the radius (see step 42), and k is incremented to have a value of 2 (step 44). The system then compares k with m and determines that k is not greater than m. It subsequently recalculates the value of DIFF using the incremented value of k (i.e. 2). The system compares U(2) with U(4) to produce a DIFF value (step 40). This value of DIFF is checked in step 42 and equals zero and accordingly, is not greater than r. Then k is incremented again (step 44), but this time, k is greater than m. With k being greater than m (as checked in step 46), step 48 is performed which increments the value at IC(1) from 1 to 2. The value of DIFF is recalculated for the corresponding values a subpattern length away from the most recently compared values (step 50). In the current case, U(3) is compared with U(5). This difference is not greater than r (see step 52); so, the value at ID(1) is incremented from 1 to 2.

Once ID(1) has been incremented, the value of j is also incremented (step 38). The result is that DIFF is calculated between U(1) and U(4) (step 40). Because the absolute value of the difference is greater than the radius, the value of j is incremented once again. With j having a value of 5, the comparison between U(1) and U(5) computes a DIFF value, equal to zero (step 46), that is within the radius (step 42). The values at U(2) and U(6) are next compared. Because the absolute value of the difference (equal to zero) is less than or equal to the radius (step 42) and k is greater than m (see step 46) after being incremented, the value at IC(1) is incremented from 2 to 3 (step 48). Furthermore, DIFF is calculated, but it is calculated between U(3) and U(7) (step 50). This absolute value of the difference is less than the radius (i.e. equal to zero as checked in step 52). As a result, the system increments the value at ID(1) from 2 to 3 (step 54). This entire process is repeated until j equals 10 which is the nsum value for the current example. At this point, the ID(1) and IC(1) computation is concluded; both ID(1) and IC(1) equal 5. The process is then repeated with i set at 2 as opposed to 1, and it is further repeated for the remaining values of i up to nsum. For this example, at the end of the computation, each element of the ID and IC arrays has the value 5.

The above described process basically compares contiguous subsets or subpatterns of the data. It first chooses a value at U(i) and finds a U(j) for which the difference between U(i) and U(j) is within the radius, r. Because, in the example, the radius is 0.5 and the example has only integer values, U(i) and U(j) must be identical to lie within the stated radius. Hence, by comparing U(i) with U(j), the system checks for those values in the data that are identical to U(i).

Once an identical value is found, the system checks the next values in the respective subpatterns of data of the values that were just compared to see if they are also identical. When i equals 1 the first subpattern of data is comprised of U(1) and U(2). In the example case, U(1) and U(2) are not identical so U(1) is compared with U(3). This comparison reveals that they are identical. The system as described above then compares the next value in the respective subpatterns: U(2) and U(4). In the above described example these two are identical; hence, the matrix location IC(1) is incremented. IC(1) keeps track of the number of subpatterns identical to the subpatterns that start at U(1). The system, however, performs an additional type of comparison. It also wants to see if the next value that succeeds the subpattern containing U(i) is identical to the next value that succeeds the subpattern containing U(j). If those values are identical, the counter memory location ID(i) is incremented. ID(i) can, thus, fairly be said to check for an additional level of patternness in the data.

When both of the loops have been completed the arrays IC(i) and ID(i) have been fully created. Each location contains the number of matches for each respective i value. The system utilizes these arrays to calculate a ratio which is determined for each i. The ratio equals the ID(i) value divided by the IC(i) value. The logarithm of the ratio is then taken for each i, and the resulting logarithms are summed. This sum is divided by the number of data values (i.e. nsum). The resulting value is equal to the average of the logarithms of the ratios. To produce a positive result, the average is multiplied by −1 to produce the approximate entropy measure.

This calculation determines the appropriately averaged relationship between the ID(i)'s and the IC(i)'s for all i. Heuristically, approximate entropy measures the (logarithmic) likelihood that runs of patterns that are close remain close on next incremental comparisons. The IC(i)'s measures the regularity (or frequency) of similar patterns; the ID(i)'s measure the stability of these patterns upon incrementing.

The calculation of the approximate entropy measure in the example case of FIG. 2A produces a value of zero. The data in FIG. 2A are completely patterned so the ratio of IC to ID equals 1, for every i, and the log of one equal zero. Thus, the approximate entropy measure equals the sum of a number of zeroes, or zero. In this example, the approximate entropy measure appropriately validates the intuitive conclusion: the completely patterned data produces an approximate entropy value of zero. In contrast, if the data is completely random, and given by white noise, the approximate entropy approaches infinity (as nsum approaches infinity).

FIG. 2B shows an "intermediate" example set of data. In this data set, every third slot is preset, with alternating values of 1 and 0 (U(3)=1, U(6) =0, U(9)=1, U(12)=0, . . .). All other slots have either 0 or 1 in them such that the value a slot has is randomly chosen, probability ½ of either 0 or 1. A computation can be performed similar to the one performed above for the example illustrated in FIG. 2A. For set parameter values of m≧3 and r <1, the approximate entropy of the sequence is computed to equal (⅔) In (2). This result is again consistent with intuition, in the following sense. The approximate entropy (⅔) In (2) is greater than 0, and the sequence in FIG. 2B appears more random, and less patterned than the sequence in FIG. 2A (which yielded the approximate entropy value of 0). In contrast, the sequence in FIG. 2B has a certain measure of patternness, given by the alternating 0's and 1's in every third location. One would expect the sequence to have lower approximate entropy than the sequence consisting entirely of random 0's and 1's in all slots. Indeed, this lastly defined sequence has approximate entropy equal to in (2), larger than (⅔) In (2), again confirming intuition. The consistency of the approximate entropy equation with intuition is another important property of this new measure for practical utility.

The above analysis can readily be expressed in mathematical terms. To express the method in such terms, let the input data be a time series denoted as U(i) where i is an index of time that goes from 1 to N. From the U(i), sequences of vectors X(i) are defined by setting X(i)=[U(i), . . . , U(i+m-1)] where m equals run or subpattern length. In the example illustrated in FIG. 2A, X(l) equals [U(1), U(2)], X(2) equals [U(2), U(3)], etc. The vector sequence X(i) can be thought of as the previously discussed runs used in the comparisons. Let $C_i^m(r)$ equal the number of X(i); such that the difference between X(i) and X(j) is less than or equal to the radius r, divided by the number of vectors in the data, N-m+1. The difference between the vectors X(i) and X(j) is defined as the maximum of the differences of their respective scalar components. $C_i^m(r)$, thus, counts the number of runs that match (i.e. fall within the tolerance) and divides this number of matches by the number of vectors. Knowing $C_i^m(r)$, one then defines $\Phi^m(r)$ as $$\varphi^m(r) = (1/N - m + 1) \sum_{i=1}^{N-m+1} \log C_i^m(r). \tag{2}$$

From Equation 2, it is clear that $\Phi^m(r)$ is equal to an average of the logarithms of the $C_i^m(r)$ for i=, . . . ,N-m+1.

The approximate entropy measure is defined as:

$$\text{approximate entropy} = \Phi^m(r) - \Phi^{m+1}(r) \tag{3}$$

where m, r and N are all fixed. From the previously disclosed equations, the approximate entropy measure can be rewritten by substituting equations for the $\Phi$'s such that $$ApEn = \frac{1}{N-m+1} \left( \sum_{i=1}^{N-m+1} \log C_i^m(r) - \log C_i^{m+1}(r) \right). \tag{4}$$

Equation 4 yields a single value for approximate entropy. The value is in the range of zero to infinity. An approximate entropy equal to zero indicates that the system is completely patterned. An approximate entropy value greater than zero indicates that the system is somewhat unpatterned. Further, higher values of ApEn imply lesser degrees of patternness. Thus, the present invention allows one to compare sets of data to determine which exhibit a greater degree of patternness.

The ApEn equation requires that two input parameters, m and r, be set; m is the "length" of compared runs, and r is effectively a filter. It must be emphasized that m and r are fixed for a given application of ApEn. ApEn values can vary significantly with m and r for a given system. A valuable property of ApEn is that it is finite for stochastic processes, whereas K-S entropy is usually infinite; thus ApEn can potentially distinguish versions of stochastic processes from each other, while entropy would be unable to do so.

Most important, despite the apparent similarities between ApEn and the K-S algorithm, ApEn is not intended as an approximate value of KolmogorovSinai entropy. It is essential to consider ApEn as a family of statistics; system comparisons are intended with fixed m and r. For a given system, there is usually significant variation in ApEn over the range of m and r. Furthermore, ApEn is a biased statistic; the average value of ApEn increases with increasing N. Thus for controlled comparisons between two groups, N must be fixed.

As mentioned above, it is crucial, in developing a patternness measure, to produce an equation that is both computable in finite time and robust to the contribution of noise. The fixing of m, the run length or length of a template pattern, as a small integer value, insures computation in finite time in the present invention. The robustness is obtained by careful choice of a value of the radius or tolerance level (r). In choosing r one must consider that noise can dramatically affect the resulting computation if r is chosen too small. In K-S entropy, the entropy is calculated as r approaches zero and, as such, noise dominates the computation, adding significantly to the level of entropy that is measured. In the present invention, the radius r is fixed so as to minimize the effects of the noise in the data on the computation. Specifically, noise well below r has negligible effect on ApEn. It should be reemphasized, however, that r provides ApEn as a relative measure of patternness at a prescribed tolerance level.

FIG. 4 illustrates a comparison of the effects of using approximate entropy on different waveforms as opposed to established measures. Suppose that the data sought to be analyzed ideally represents a discrete sampling from a perfect sine wave as shown in FIG. 4A. Suppose, however, that a small amount of noise corrupts the data as in FIG. 4B. The effect of this noise on an established entropy calculation is great. It dramatically alters the result. The mean and standard deviation are hardly affected, nor is the approximate entropy measure significantly affected. Suppose, however, that the data is like the data shown in FIG. 4C with large errors. The mean and standard deviation are greatly affected. Both entropy and approximate entropy are, in contrast, nearly unaffected. Thus, the present invention obtains the best aspects of both types of established measures.

The input data for ApEn is a scalar time-series, with typically between 100 and 5000 numbers. Fewer than 100 numbers will likely yield a less meaningful computation, especially for m=2 or m=3. Values of m=1, 2 or 3 are generally chosen.

The present invention filters out the noise by choosing a value of r such that the contribution of noise to the entropy calculation is minimized. A balance is sought in choosing r. If r is too small, noise will corrupt the approximate entropy calculation. If r is too large, too much "fine detail" will be lost to the coarseness of the filter. A range for r that appears to be desirable, and that has performed well in studies such as the neonatal study described earlier, is $0.1\sigma$ to $0.25\sigma$ where $\sigma$ is a standard deviation of the data. These values of r are usually effective in distinguishing data sets. Noise in the data much smaller than r is effectively filtered out in the ensuing calculation.

Heartbeat Data

Figure 5:
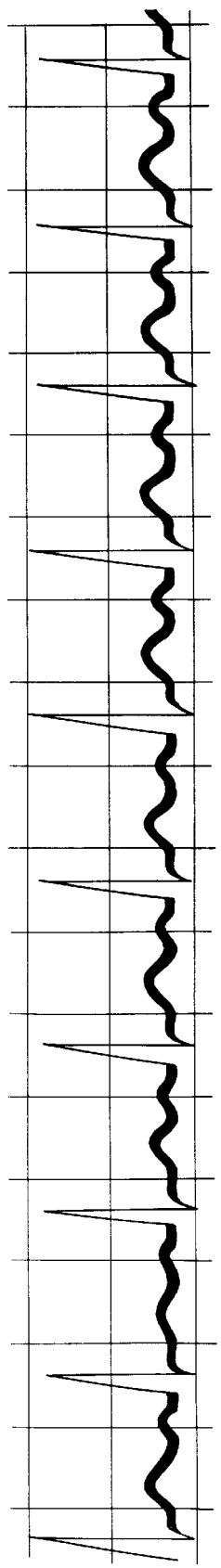
FIG. 5 shows a sample EKG tracing.
Figure 6:
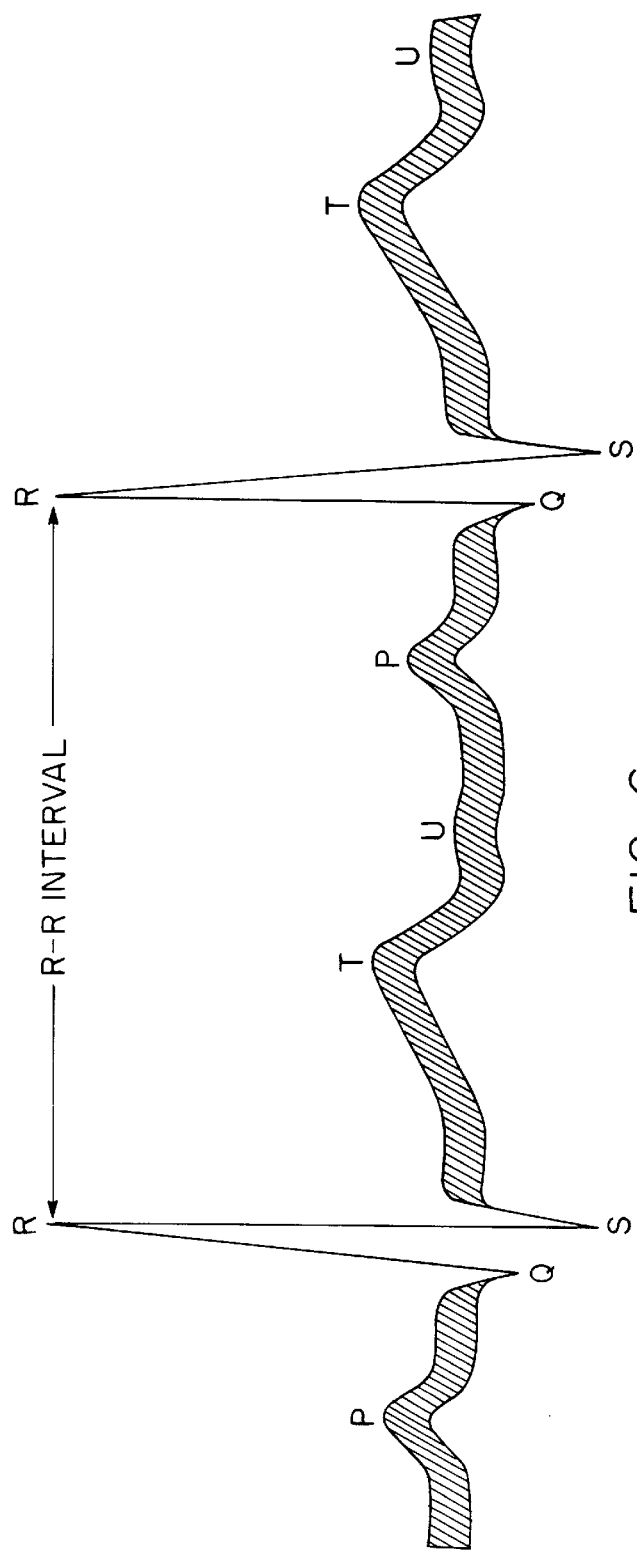
FIG. 6 shows two sample pulses of a heartbeat.

Approximate entropy, applied to heartbeat data, can potentially be used as a general barometer of human health. In particular, the data processing system looks at the interbeat intervals in EKG tracings. FIG. 5 shows a typical EKG tracing for a healthy heart. The interbeat intervals are measured between the R-portions of consecutive pulses. Two consecutive pulses, and the R—R interval for them, are shown in FIG. 6.

Approximate entropy has already been found to distinguish sick neonates from healthy neonates in a study conducted by one of the inventors at the Yale University School of Medicine. In this study, performed with two faculty pediatricians, data were taken for 15 healthy neonates and 9 asphyxiated neonates. Their heart rates were averaged every 5 seconds, for 1000 measurements. The approximate entropy was lower for the sick group, as anticipated, corresponding to greater patternness. The sick group had an approximate entropy average of 0.80±0.31 versus 1.22±0.12 (mean±1 S.D.) for healthy neonates. The significance of this result was p=0.003 (t-test). Comparisons between the two groups, using the clinically used measure of heartbeat variability, VAR (standard deviation) did not show a significant difference between the two groups (p=0.14). Tables 1a and 1b show the data from this study for both the healthy and sick groups, respectively. Moreover, a serial study on a septic infant with persistent pulmonary hypertension showed a large steady increase in approximate entropy with recovery, further confirming approximate entropy as a barometer of general health. Additionally, approximate entropy discerned the poor health of several of the infants who were otherwise without recognizable EKG abnormalities.

Moreover, ApEn is useful in monitoring fetal heart data to indicate fetal distress, in indicating high-risk infants susceptible to sudden infant death syndrome (SIDS) by monitoring the heart-rate data of the infant, as a marker of aging, and in indicating risk for adverse cardiac events following surgery. Furthermore, the approximate entropy measure can be used to determine subtle arrhythmias that are not otherwise detectable.

TABLE 1a

TABLE OF RESULTS (HEALTHY)

| HEALTH | ApEn | VAR | WT (GMS.) | AGE (WKS.) | SEX |
|---|---|---|---|---|---|
| 1. HEALTHY | 0.94 | 5.57 | 2050 | 36 | M |
| 2. HEALTHY | 1.08 | 6.99 | 1750 | 33 | F |
| 3. HEALTHY | 1.11 | 6.69 | 2010 | 31 | M |
| 4. HEALTHY | 1.12 | 10.29 | 1890 | 33 | F |
| 5. HEALTHY | 1.16 | 8.13 | 1800 | 34 | F |
| 6. HEALTHY | 1.20 | 9.42 | 550 | 24 | F |
| 7. HEALTHY | 1.24 | 8.53 | 1820 | 37 | F |
| 8. HEALTHY | 1.25 | 17.65 | 2020 | 41 | M |
| 9. HEALTHY | 1.27 | 8.56 | 3650 | 40 | M |
| 10. HEALTHY | 1.27 | 11.08 | 1300 | 34 | F |
| 11. HEALTHY | 1.29 | 11.95 | 1600 | 36 | F |
| 12. HEALTHY | 1.30 | 10.31 | 1730 | 33 | F |
| 13. HEALTHY | 1.30 | 9.54 | 3490 | 40 | F |
| 14. HEALTHY | 1.38 | 14.31 | 3100 | 40 | M |
| 15. HEALTHY | 1.40 | 15.10 | 4360 | 42 | M |

SUMMARY STATISTICS: (MEAN +/- SD)

ApEn: 1.22 +/- 0.12
VAR: 10.27 +/- 3.33
WT: 2210 +/- 1000
AGE: 35.6 +/- 4.7

TABLE 1b

TABLE OF RESULTS (SICK)

| HEALTH | ApEn | VAR | WT (GMS.) | AGE (WKS.) | SEX |
|---|---|---|---|---|---|
| 1. CONG. HF | 0.32 | 4.34 | 2430 | 34 | M |
| 2. PPH | 0.46 | 6.56 | 1090 | 27 | M |
| 3. PPH | 0.59 | 7.37 | 1090 | 27 | M |
| 4. CONG. HF | 0.69 | 10.49 | 3810 | 37 | F |
| 5. SEVERE RDS | 0.73 | 8.13 | 870 | 26 | M |
| 6. PPH | 1.02 | 11.70 | 1090 | 27 | M |
| 7. CONF. HF, DIAPH. HERN. | 1.03 | 7.88 | 2670 | 39 | M |
| 8. CONG. HF (TRI. 18) | 1.15 | 11.61 | 2270 | 39 | F |
| 9. GI OBST., TEF/Asp | 1.19 | 8.24 | 2640 | 40 | F |

| | |
|---|---|
| CONG. HF: | CONGENITAL HEART FAILURE |
| DIAPH. HERN.: | DIAPHRAGMATIC HERNIA |
| GI OBST.: | GASTROINTESTINAL OBSTRUCTION |
| PPH: | PERSISTENT PULMONARY HYPERTENSION |
| RDS: | RESPIRATORY DISTRESS SYNDROME |
| TEF/Asp: | TRACHEO-ESOPHAGEAL FISTULA WITH ASPIRATION |
| TRI. 18: | TRISOMY 18 |

TABLE 1b-continued

TABLE OF RESULTS (SICK)

| HEALTH | ApEn | VAR | WT (GMS.) | AGE (WKS.) | SEX |
|---|---|---|---|---|---|

SUMMARY STATISTICS: (MEAN +/- SD)

ApEn: 0.80 +/- 0.31
VAR: 8.48 +/- 2.42
WT: 2000 +/- 1010
AGE: 32.9 +/- 6.1

Hormone Secretion Study

A study was performed to examine the potential applicability of ApEn to clinical endocrinology, and to quantify pulsatility in hormone secretion data. The study evaluated the role of ApEn as a complementary statistic to widely employed pulse detection algorithms, represented herein by ULTRA (Van Cauter, E., "Quantitative Methods for the Analysis of Circadian and Episodic Hormone Fluctuations," In *Human Pituitary Hormones: Circadian and Episodic Variations,* edited by E. Van Cauter and G. Copinschi, The Hague:Martinus Nyhoff, 1981: 1–25), via the analysis of two different classes of models that generate episodic data. ApEn is able to discern subtle system changes and to provide insights separate from those given by ULTRA. ApEn evaluates subordinate as well as peak behavior, and often provides a direct measure of feedback between subsystems. ApEn generally can distinguish systems given 180 data points and an intraassay coefficient of variation of 8%. Additionally, the models and the extant clinical data are both consistent with episodic, not periodic, normative physiology. Thus, approximate entropy (ApEn), as a statistic, is applicable to hormone secretion data.

Given the presence of a non-trivial amount of noise, there are two steps in performing hormone secretion pulse analysis. The first is separating the "true" secretion time-series from the noise. The second step is in evaluating the resulting "true" time-series. While these two steps are typically commingled in each algorithm, this is a complementarity between ApEn and the pulse-identification algorithm, due to their different approaches to the second step. ApEn summarizes the time-series by a single number, whereas the pulse-identification algorithms identify peak occurrences and amplitudes. ApEn discerns changes in underlying episodic behavior that do not reflect in changes in peak occurrences or amplitudes, while the pulse-identification algorithms ignore such information.

Implicit to current models of hormone release is a periodicity assumption, with deviations attributed to noise. Two models which are capable of generating by themselves episodic, but not periodic, data are presented herein. In each model, there are several parameters that are varied, to generate a variety of data sets. For each model, ability of ApEn and a widely-used pulse-identification algorithm, ULTRA, to distinguish among the data sets generated by these models is evaluated. It is not suggested that these models represent known physiological systems, but rather these are offered as representative of alternative hypotheses to be considered when explaining observed episodic hormonal secretion. The present focus is not to propose a model that best mimics physiological reality, but rather to propose a new use of a statistic that gives different insights than are given by pulse-counting algorithms.

Episodic Hormone Secretion

Episodic, or pulsatile, secretion of hormones is an increasingly general finding in endocrinology. With the availability of sensitive radioimmunoassays (RIAs), which require only small sample volumes, protocols employing frequent sampling became possible. Furthermore, methods which help distinguish assay noise from biological variability make pulse detection a more rigorous endeavor. Studies employing such techniques in humans and diverse animal species have characterized pulsatile secretion of a large number of hormones, including luteinizing hormone (LH), insulin, progesterone, glucagon, growth hormone, ACTH, cortisol, prolactin, aldosterone, and HCG.

Elucidating the secretory patterns of hormone release has not only shed light on endocrine physiology, but also clarified the pathophysiology and improved the treatment of some diseases. For example, derangement in the episodic secretion of LH underlies some common disorders in humans, such as polycystic ovary syndrome, and hypogonadotropic hypogonadism. Administration of LHRH in a periodic fashion, designed to produce a normal LH secretory pattern, improved the pharmacologic therapy of these disorders. Similarly, elucidation of pulsatile insulin secretion in normal subjects laid the groundwork for the discovery of abnormal insulin secretory patterns on diabetic, and improved the efficacy of insulin replacement therapy by administration of the hormone in a periodic fashion.

Current Pulse-Identification Algorithms

The tools currently employed by endocrinologists to analyze the pulsatility of hormone secretion data fall under the aegis of peak-identification algorithms. The philosophy of these methods is to identify the "true" peaks in the data, distinct from apparent peaks generated by the random variations due to assay imprecision. Once these true peaks are identified, one may be able to determine normal and abnormal ranges of pulse frequency, amplitude, and duration, and hence potentially identify abnormal secretion. There are considerable differences among the algorithms, due to a variety of approaches in handling the intraassay noise. This intraassay variation typically has a coefficient of variation (CV) of between 6% and 14% (e.g., Fuchs, A. R., K. Goeschen, and P. Husslein, "Oxytocin and the Initiation of Human Parturition III: Plasma Concentration of Oxytocin and 13, 14-dihydro-15 Keto-prosaglandin F2-alpha in Spontaneous and Oxytocin-Induced Labor at Term,"*Am. J. Obstet. Gynecol.* 147 (1983): 497–502), an amount of noise that can in some instances make true peak detection very difficult. Nonetheless, for all of these algorithms, in the absence of noise, (i) one achieves identical peak detection, and (ii) changes in subordinate patterns that do not result in new or altered peaks are ignored.

The following eight pulse-detection programs are among those most widely available and extensively employed: Santen and Bardin (Santen, R. J., and C. W. Bardin, "Episodic Luteinizing Hormone Secretion in Man: Pulse Analysis, Clinical Interpretation, Physiologic Mechanisms," *J. Clin. Invest.* 52 (1973):2617–2628); modified Santen and Bardin; ULTRA; PULSAR (Merriam, G. R., and K. W. Wachter, "Algorithms for the Study of Episodic Hormone Secretion," *Am. J. Physiol.* 243 (1982): E310–318); Cycle Detector (Clifton, D. K., and R. A. Steiner, "Cycle Detection: A Technique for Estimating the Frequency and Amplitude of Episodic Fluctuations in Blood Hormone and Substrate Concentrations;" *Endocrinology* 112 (1983): 1057–1064), Regional Dual Tbreshold (Veldhuis, J. D., J. Weiss, N. Mauras, A. D. Rogol, W. S. Evans, and M. L. Johnson, "Appraising Endocrine Pulse Signals at Low Circulating Hormone Concentrations: Use of Regional Coefficients of Variation in the Experimental Series to Analyze Pulsatile Luteinizing Hormone" Release. *Pediatr. Res.* 20 (1986):632–637), Cluster (Veldhuis, J. D., and M. L. Johnson, "Cluster Analysis: A Simple, Versatile, and Robust Algorithm for Endocrine Pulse Detection," *Am. J. Physiol.* 250 (1986): E486–493); and Detect (Oerter, K. E., V. Guardabasso, and D. Rodbard, "Detection and Characterization of Peaks and Estimation of Instantaneous Secretory Rate for Episodic Pulsatile Hormone Secretion," *Comput. Biomed. Res.* 19 (1986):170–191). The similarity of the pulse-identification algorithms in the presence of negligible noise, the apparent relative robustness to non-trivial CVs, the usefulness with 50 to 200 data points, and the philosophy of peak analysis as the means to evaluate pulsatility bond this class of algorithms together. ULTRA has been chosen as representative of these algorithms in performing the comparisons with ApEn below. It is expected that another choice of pulse-detection algorithm, for the purpose of comparison with ApEn, would give quite similar results.

Based on published time-series of hormonal concentration levels, there is the need for an added dimension in the analysis of episodic hormone release, beyond monitoring the pulse count and related statistics. Lang et al., (Lang, D. A., D. R. Matthews, and R. C. Turner, "Brief, Irregular Oscillations of Basal Plasma Insulin and Glucose Concentrations in Diabetic Men," *Diabetes* 30 (1981): 435–439) conclude that brief, irregular oscillations in plasma insulin levels, in maturity-onset diabetics, are superimposed on longer term oscillatory fluctuations commonly observed in the nondiabetic. ApEn provides a quantification of the regularity of these data, which is useful for distinguishing a diabetic's insulin secretion patterns from those of a non-diabetic.

Furthermore, episodic variation in hormones often has revealed complex patterns, challenging existing programs to characterize, and then differentiate, a "diseased" pattern from a healthy one. Finally, frequency distributions of discrete LH pulse properties, given by Urban (Urban, R. J., W. S. Evans, A. D. Rogol, D. L. Kaiser, M. L. Johnson, and J. D. Veldhuis, "Contemporary Aspects of Discrete Peak-Detection Algorithms: I. The paradigm of the Luteinizing Hormone Pulse Signal in Men," *Endocrine Revs.* 9 (1988): 3–37) and based on nearly 200 pulses, show significantly non-Gaussian distributions for both pulse frequencies and amplitudes. The asymmetry of these distribution is not consonant with the typical assumption of periodic pulses in the presence of symmetrically distributed noise. One thus either concludes a lack of periodicity in these LH pulses, or at least must entertain the possibility of such a periodicity in constructing algorithms to analyze such series.

The crucial difficulty in applying conventional entropy measurements to hormone secretion data is that hormone secretion data are relatively few in number (at most, several hundred data points), whereas an accurate conventional entropy calculation for an underlying system of dimension d typically requires from $10^d$ to $30^d$ data points (Wolf, A., J. B. Swift, H. L. Swinney, and J. A. Vastano, "Determining Lyapunov Exponents from a Time-Series," *Physica* 16D (1985):285–317). The number of data points is key, because there is no reason to anticipate, and no evidence to show, that data typically encountered from such complex interacting systems of glands and hormones that form endocrine systems be low-dimensional. Furthermore, one cannot assume that hormonal secretion is correctly modelled by deterministic chaos, as opposed to a stochastic model.

ApEn has many of the characteristics deemed important for effective characterization of episodic hormone release as described by Urban et al. ApEn is objective, simple to use, via existing FORTRAN and C-language computer programs, and ApEn produces a single number. ApEn has minimal dependence on the specific type of signal or noise present in the underlying data. ApEn is versatile; it can be used for any time-series data analysis, to compute a measure of regularity. For hormone pulse detection, ApEn is readily adaptable to differences in sampling frequency and duration, assay performance, and signal-noise ratios. ApEn is very stable to small changes in noise characteristics, infrequent and significant data artifacts, and changes in sampling frequency. ApEn is concordant with visual inspection. ApEn accounts for a variety of dominant and subordinate patterns in data; notably, ApEn is affected by changes in underlying episodic behavior that do not reflect in changes in peak occurrences or amplitudes.

Additionally, ApEn provides a direct barometer of feedback system change in some coupled systems. Thus, ApEn is useful in shedding insight into interactions among hormones, indicating a source of underlying physiologic deviations, such as a breakdown in the normal system feedback process.

Model Comparison Framework

Results from ApEn and ULTRA calculations for test data from two models are discussed below. To calculate ApEn and ULTRA for these data, certain inputs in each algorithm must be specified. For ApEn, m is set to 2 throughout the models, and r is chosen, fixed for each model, to equal about 20% of the standard deviation of a typical data set. This results in choices of r=0.4 for the Ueda model and r=0.1 for the Rossler model, consistent with guidelines given by Pincus (Pincus, S. M., I. M. Gladstone, and R. A. Ehrenkranz, "A Regularity Statistic for Medical Data Analysis," *J. Clin. Monit.* 7(4) (October 1991): 335–345)

For ULTRA, 3 CVs are chosen as the threshold for the Ueda model, and 2 CVs are chosen as the threshold for the Rossler model. This is consistent with Van Cauter's guidelines (applied to the "predominant" pattern in each instance). To determine concentration ranges and CV values for each range, one works backwards from the noise standard deviation data given in each version of each model. In each version, there is a model in which Gaussian noise of a fixed standard deviation (sdev) is superimposed on all the data, to model the inaccuracy of assay measurements. The output concentration ranges, for each time series, is divided into 8 pieces, each with a mean m. For each range, the CV is set to be sdev/m.

The output of ApEn is a number, while the output of ULTRA is an identified set of peaks of pulses in the data. From each ULTRA output, the number of pulses, the average and standard deviation of pulse lengths, and the average and standard deviation of pulse amplitudes are calculated. For each model, a table is used to summarize the runs. Each line in the tables lists the run number, number of data points in the time series, and input model characteristics: parameter choices, and standard deviation of superimposed Gaussian noise. The output data includes the mean and standard deviation of the time series, ApEn value, number of pulses, and mean and standard deviation for both pulse frequency and pulse amplitude.

Ueda Differential Equation Model

Figure 7A:
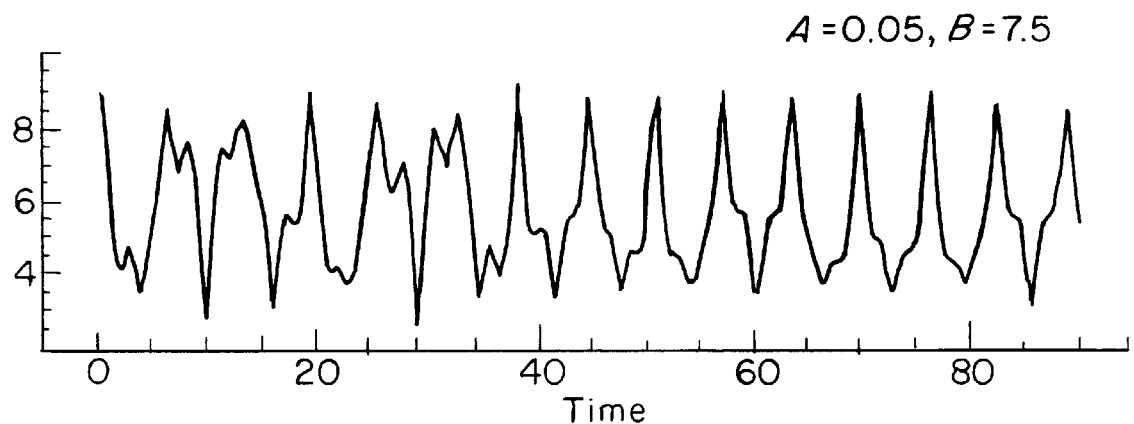
FIGS. 7A–C are Ueda differential equation model time-series output for three pairs of parameter values.
Figure 7B:
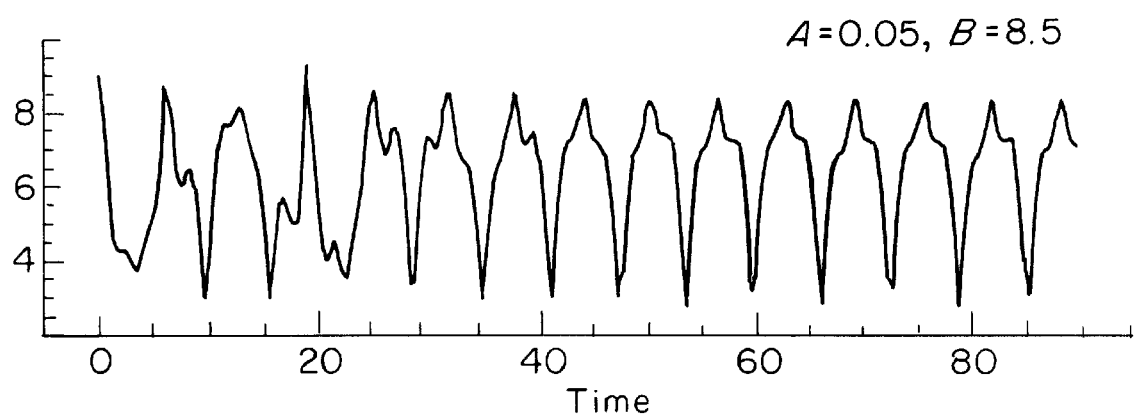
Figure 7C:
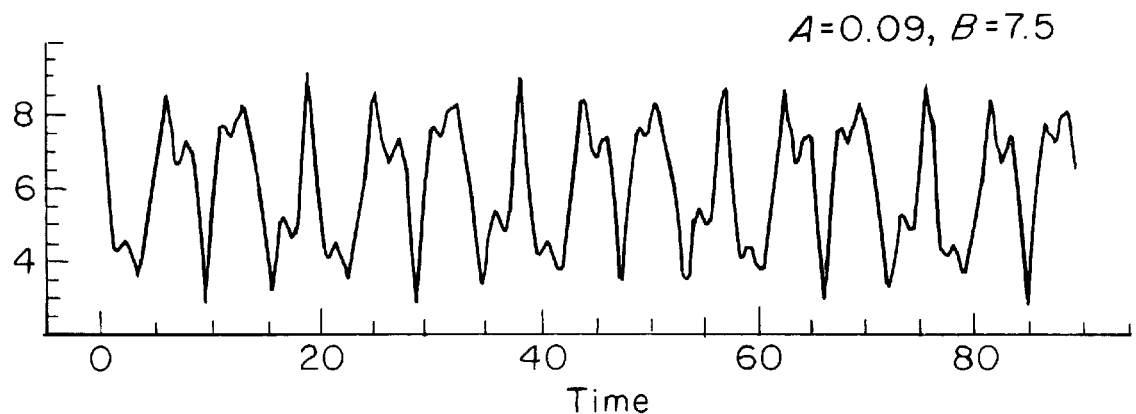

The equation $$\ddot{x} + A\dot{x} + x^3 = B\cos t$$

is a differential equation that has received considerable attention in recent years, due in great part to studies by Ueda (Ueda, Y., "Steady Motions Exhibited by Duffing's Equation: A Picture Book of Regular and Chaotic Motions," In *New Approaches to Nonlinear Problems in Dynamics,* edited by P. J. Holmes, Philadelphia, Pa.:SIAM, 1980: 311–322) showing that the long-term dynamics of the solution represent steady-state chaotic behavior, for parameter values A=0.05, B=7.5. This equation, where the dots denote differentiation with respect to time t, describes the behavior of the variable x over time; for each time, the corresponding value of x can be calculated (via numerical methods), to deduce a time-plot of x as illustrated in FIGS. 7A–C. Equation 5 may be used in mechanical engineering, e.g., to model the motion of a sinusoidally forced structure undergoing large elastic deflections. The solution is bounded, episodic, yet nonperiodic.

Here, Equation 5 is analyzed for five (A,B) pairs: (0.05, 7.5), (0.05, 8.5), (0.05, 12.0), (0.09, 7.5), and (0.21, 7.5). For each pair, equation 5 is solved as a function in time by an explicit time step method, $\Delta t=0.002$. A time series is extracted from the solution by sampling every 0.5 t-units. This sampling rate was chosen to yield about 12 data points per episode, and generates the baseline series. This is consistent with Yates, (Yates, F. E., "Analysis of Endocrine Signals: The Engineering and Physics of Biochemical Communication Systems", *Bio. Reprod.* 24 (1981): 73–94), where samples of at least 6 times the expected frequency are seen as necessary to deduce periodicities, and with Veldhuis (Veldhuis, J. D., W. S. Evans, A. D. Rogol, C. R. Drake, M. O. Thorner, G. R. Merriam, and M. L. Johnson, "Intensified Rates of Venous Sampling Unmask the Presence of Spontaneous, High Frequency Pulsation of LH in Men," *J. Clin. Endocrinol. Metab.* 59 (1984): 96–102), which notes the clinical need for intensified sampling rates. The solution time-series is post-processed by converting x to x+6.0 for all data values. This is done to ensure positive values, in the range 3.0 to 9.0, to mimic endocrine data. Uniform white noise is added to each baseline value to deduce the final series. For each pair, two different lengths of series are analyzed, 180 points and 900 points. For (0.05, 7.5) and (0.05, 8.5), the series is analyzed with 2000 points.

This model is analyzed for two primary reasons. First, the model exemplifies a simple system which gives rise to highly nontrivial, putatively pulsatile behavior. Second, the model forces a careful examination of the meaning of pulsatility, to ensure that the quantitative tools used reasonably correspond to intuitive expectations. The crucial property of the solution to the Ueda equation is that it is episodic, but truly non-periodic. The equation's recurrent nature is evidenced by the fact that certain patterns in the waveform repeat themselves at irregular intervals, but there is never exact repetition. There is an apparent baseline frequency per episode (pulses), though there is temporal variation of a non-periodic nature. Furthermore, there are second-order, irregularly varying wiggles in the episodes that are generated by the model itself.

This system is an appropriate model for hormone secretion, with normal secretion given by a model with A and B as stated above fixed, with A=0.5, and B between 8.5 and 12.0. On the basis of time-series data alone, the system can detect that certain data came from an "abnormal" system for which A=0.5 and B=15.0.

As reported by Table 2, runs 1–10, the pulse count for noiseless systems is given as half the number of sign changes. This property is common to many of the current pulse identification algorithms, in which a pulse is flagged as a measured rise and fall, with both the rise and fall indicated by some percentage rise and fall times the noise level.

TABLE 2

ULTRA Statistics

| Run No | No. of Points | Ueda Parameters K | B | Input Noise SD | Mean | SD | ApEn | No. of Sign Changes | No. of Pulses | Avg. Freq. | SD Freq. | Avg. Amp | SD Amp |
|---|---|---|---|---|---|---|---|---|---|---|---|---|---|
| 1 | 180 | 0.05 | 7.5 | 0.0 | 5.808 | 1.593 | 0.677 | 56 | 28 | 6.185 | 2.450 | 7.368 | 1.834 |
| 2 | 180 | 0.05 | 8.5 | 0.0 | 6.401 | 1.612 | 0.543 | 50 | 25 | 6.792 | 3.400 | 7.771 | 1.276 |
| 3 | 180 | 0.09 | 7.5 | 0.0 | 6.074 | 1.650 | 0.574 | 66 | 33 | 5.406 | 1.292 | 7.363 | 1.596 |
| 4 | 180 | 0.05 | 12.0 | 0.0 | 5.992 | 1.781 | 0.762 | 81 | 40 | 4.410 | 1.044 | 7.406 | 1.692 |
| 5 | 180 | 0.21 | 7.5 | 0.0 | 6.174 | 1.549 | 0.676 | 46 | 23 | 7.818 | 3.390 | 7.624 | 1.338 |
| 6 | 900 | 0.05 | 7.5 | 0.0 | 5.973 | 1.597 | 0.894 | 275 | 137 | 6.463 | 2.839 | 7.476 | 1.576 |
| 7 | 900 | 0.05 | 8.5 | 0.0 | 6.533 | 1.567 | 0.466 | 213 | 105 | 8.452 | 4.031 | 8.028 | 0.769 |
| 8 | 900 | 0.09 | 7.5 | 0.0 | 6.034 | 1.637 | 0.590 | 333 | 166 | 5.388 | 1.447 | 7.335 | 1.570 |
| 9 | 900 | 0.05 | 12.0 | 0.0 | 6.068 | 1.758 | 1.153 | 401 | 200 | 4.462 | 1.131 | 7.531 | 1.540 |
| 10 | 900 | 0.21 | 7.5 | 0.0 | 5.908 | 1.550 | 0.666 | 227 | 112 | 7.991 | 3.361 | 7.635 | 1.550 |
| 11 | 900 | 0.05 | 7.5 | 0.05 | 5.971 | 1.597 | 0.904 | 281 | 117 | 7.578 | 3.492 | 7.731 | 1.486 |
| 12 | 900 | 0.05 | 7.5 | 0.1 | 5.968 | 1.599 | 0.953 | 287 | 104 | 8.534 | 3.694 | 7.925 | 1.393 |
| 13 | 900 | 0.05 | 7.5 | 0.2 | 5.963 | 1.609 | 1.091 | 299 | 97 | 9.156 | 3.675 | 8.098 | 1.250 |
| 14 | 900 | 0.05 | 7.5 | 0.4 | 5.953 | 1.647 | 1.336 | 367 | 84 | 10.59 | 3.425 | 8.417 | 0.975 |
| 15 | 900 | 0.05 | 8.5 | 0.05 | 6.530 | 1.567 | 0.473 | 213 | 77 | 11.57 | 2.568 | 8.311 | 0.611 |
| 16 | 900 | 0.05 | 8.5 | 0.1 | 6.528 | 1.569 | 0.510 | 253 | 76 | 11.72 | 2.408 | 8.320 | 0.603 |
| 17 | 900 | 0.05 | 8.5 | 0.2 | 6.523 | 1.577 | 0.742 | 289 | 78 | 11.41 | 2.769 | 8.305 | 0.613 |
| 18 | 900 | 0.05 | 8.5 | 0.4 | 6.513 | 1.614 | 1.196 | 379 | 77 | 11.57 | 2.806 | 8.479 | 0.400 |
| 19 | 900 | 0.09 | 7.5 | 0.05 | 6.031 | 1.638 | 0.602 | 333 | 165 | 5.421 | 1.486 | 7.332 | 1.575 |
| 20 | 900 | 0.09 | 7.5 | 0.1 | 6.029 | 1.640 | 0.634 | 335 | 155 | 5.773 | 1.881 | 7.371 | 1.582 |
| 21 | 900 | 0.09 | 7.5 | 0.2 | 6.024 | 1.650 | 0.909 | 339 | 121 | 7.408 | 3.245 | 7.789 | 1.390 |
| 22 | 900 | 0.09 | 7.5 | 0.4 | 6.014 | 1.687 | 1.292 | 365 | 92 | 9.769 | 3.715 | 8.340 | 1.029 |
| 23 | 2,000 | 0.05 | 7.5 | 0.0 | 6.075 | 1.597 | 0.871 | 588 | 294 | 6.782 | 3.116 | 7.544 | 1.469 |
| 24 | 2,000 | 0.05 | 8.5 | 0.0 | 6.559 | 1.556 | 0.443 | 460 | 229 | 8.715 | 4.077 | 8.069 | 0.639 |

In the absence of noise, any rise is considered a pulse ascent, and any fall considered a pulse descent. Therefore, to evaluate ULTRA as a pulse-counting algorithm, it suffices to examine the statistical properties of the algorithm that counts the number of sign changes. This statistic has been extensively examined (Sen, P. K., "Signed-Rank Statistics," *In Encyclopedia of Statistical Sciences* 8, edited by S. Kotz and N. L. Johnson. New York:John Wiley, 1988: 461–466) and provides useful information. It does not, however, utilize any information contained in the magnitudes associated with the sign changes, so that a tiny wiggle counts as much as a large wave. An instance of an improved measure is given by the Wilcoxon signed-rank statistic, a standard non-parametric statistical test. In this context, ranks would be given to the sign changes, with the largest rank to the greatest sign change. Hence, big pulses "count" more than little pulses, possibly a desired characteristic in the goal to distinguish normal from abnormal behavior.

A central issue for this model is apparent upon examination of FIGS. 7A–C. Time-series output is shown in FIGS. 7A–C for three pairs of parameter values, (a) K=0.05, B=7.5, (b) K=0.05, B=8.5, and (c) K=0.09, B=7.5, respectively. These series are apparently different, but quantitative tools to distinguish them are not a priori apparent. These series have mean approximately equal to 6, standard deviation approximately equal to 1.6. Each series has a "period" of $2\pi$, but no two periods are identical; there are different peak amplitudes, shapes, and subordinate "wiggles" throughout. Both ApEn and ULTRA distinguish versions of this model, but the results require scrutiny, because they appear to be in disagreement.

First, runs 1–10, are summarized in Table 2. They represent runs for the five K-B pairs specified above, for two series lengths, 180 points and 900 points. According to ApEn, these versions rank (from most random to least random, in descending order) as (0.05, 12.0), (0.05, 7.5), (0.21, 7.5), (0.09, 7.5), (0.05, 8.5). This order is maintained for both 180 and 900 points, although several distinctions are sharper for 900 points than for 180 points. For this model, 900 points yields good convergence for ApEn; comparing run 6 to ran 23 (900 vs. 2000 points, K=0.05, B=7.5), ApEn changes from 0.894 to 0.871. Similarly, comparing run 7 to run 24, (900 vs. 2000 points, K=0.05, B=8.5), ApEn changes from 0.466 to 0.443.

According to ULTRA, these versions rank (from most random to least random) as (0.05, 12.0), (0.09, 7.5), (0.05, 7.5), (0.21, 7.5), (0.05, 8.5). This order is nearly maintained for both 180 and 900 points, although the last two versions reverse order in the 180 and 900 point cases. Furthermore, with the exception of the (0.05, 8.5) case, a five-fold increase in point count corresponds to virtually a five-fold increase in pulse number. This ratio of pulses to points is maintained in the two 2000-point runs, hence the 900-point runs are sufficiently long to extract the salient pulse information here. However, there is an apparent conflict over which of (0.05, 7.5) or (0.09, 7.5) is more random (unpatterned).

The Poincare section is a tool to resolve this impasse. First, a phase space plot is generated (for each series), plotting the trajectory of x versus its time derivative, dx/dt. To insure a sequence of strictly comparable points, the trajectory is marked stroboscopically at times that are an integer multiple of the forcing period $2\pi$. The resulting plot, in the x-dx/dt plane, shows only the strobed points as the Poincare section. If the motion of the system were strictly periodic with the frequency of the forcing, the strobe point would all be the same point, repeating indefinitely. If the true motion were multiply periodic, then a sequence of n dots would appear, repeated indefinitely. More complicated dynamics are represented by more filled out Poincare section portraits, which correspond to greater ApEn.

It can be shown (data not shown) that FIG. 7A has the most complicated dynamics, FIG. 7C has the next most complicated dynamics, and FIG. 7B has the least complicated dynamics. This corresponds to a greatest randomness for (0.05, 7.5), then (0.09, 7.5), followed by (0.05, 8.5), the order given by ApEn. Furthermore, the respective ApEn values, 0.894, 0.590, and 0.466, seem to correspond to the intuition that the (0.09, 7.5) case is closer to the (0.05, 8.5) case in randomness than to the (0.05, 7.5) case.

The apparent inconsistency in ULTRA is explained by its equal weighting of each of many tiny wiggles and the larger sign changes. The (0.09, 7.5) case has the greatest number of sign changes of the three cases examined in FIGS. 7A–C, but these sign changes, particularly the "small wiggles," tend to occur near similar locations in each major "pulse." This can be virtually expressed by areas of darker clustering in phase portraits. Greater randomness would be marked by a greater spread of these dark clusters. The last point reemphasizes the foibles of the sign change algorithm, as opposed to a weighted sign change algorithm.

Returning to Table 2, runs 11–22 further illustrate the difficulties that these small wiggles pose for ULTRA. For each of the versions (0.05, 7.5), (0.05, 8.5), and (0.9, 7.5), four different noise levels, standard deviations of 0.05, 0.1, 0.2, and 0.4, corresponding to CVs of approximately 1%, 2%, 4%, and 8%. In the (0.05, 7.5) case, ULTRA noted 137 pulses at 0 noise, compared to 117 pulses at 0.05 noise, and 104 pulses at 0.1 noise. This represents a computational loss of about 15% of pulses at 1% CV. In the (0.05, 8.5) case, ULTRA noted 105 pulses at 0 noise, compared to roughly 77 pulses in the presence of at least 0.05 noise. These 77 pulses represent, almost solely, the large pulses of approximate duration $2\pi$. Virtually all the small wiggles were effectively ignored in the presence of the noise levels noted above. This represents a computational loss of about 27% of pulses at 1% CV. In the (0.09, 7.5) case, ULTRA behaved more robustly at low noise levels, with 166 pulses at 0 noise, 165 pulses at 0.05 noise, and 155 pulses at 0.1 noise.

ApEn performs more robustly at low noise levels. In the (0.05, 7.5) case, ApEn is 0.894 at 0 noise, 0.904 at 0.05 noise, and 0.953 at 0.1 noise. In the (0.05, 8.5) case, ApEn is 0.466 at 0 noise, 0.473 at 0.05 noise, and 0.510 at 0.1 noise. In the (0.09, 7.5) case, ApEn is 0.590 at 0 noise, 0.602 at 0.05 noise, and 0.634 at 0.1 noise. These all represent about a 1% to 2% change at 1% CV, and a 7% to 9% change at 2% CV.

Figure 8A:
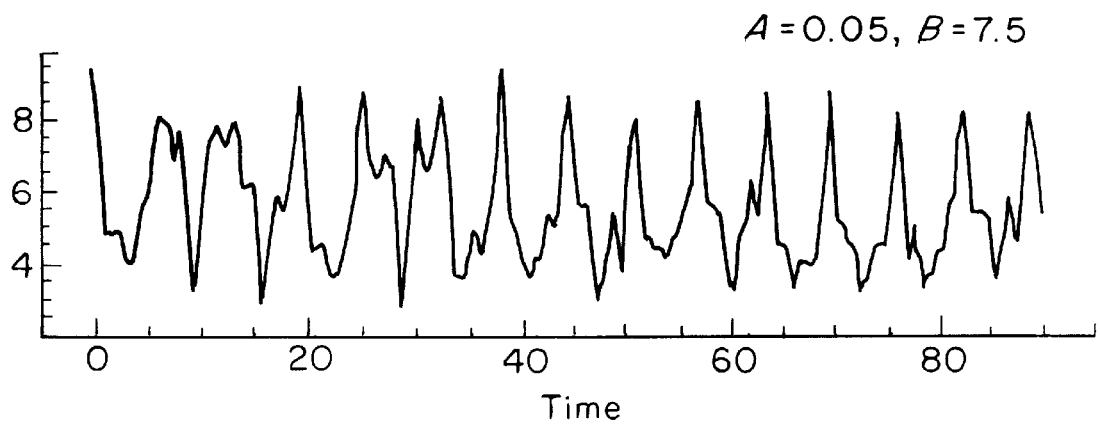
FIGS. 8A–C are Ueda differential equation model time-series output with Gaussian noise superimposed for the parameter values of FIGS. 7A–C.
Figure 8B:
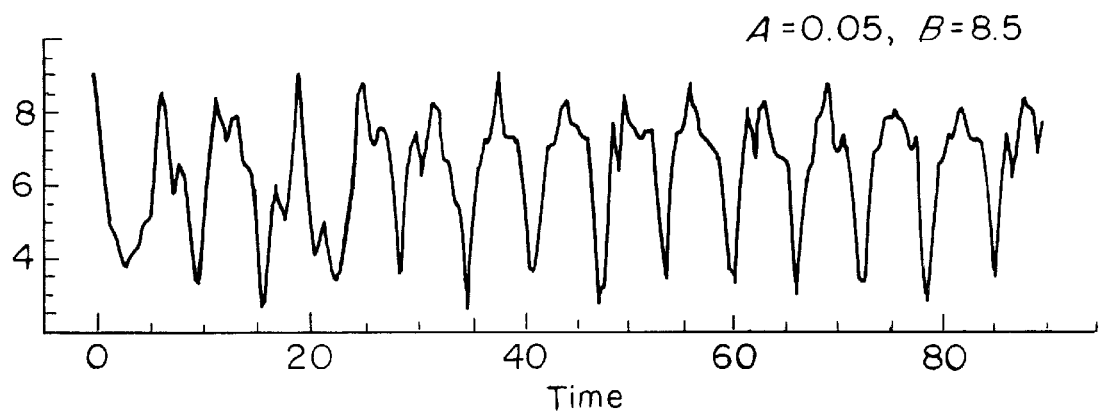
Figure 8C:
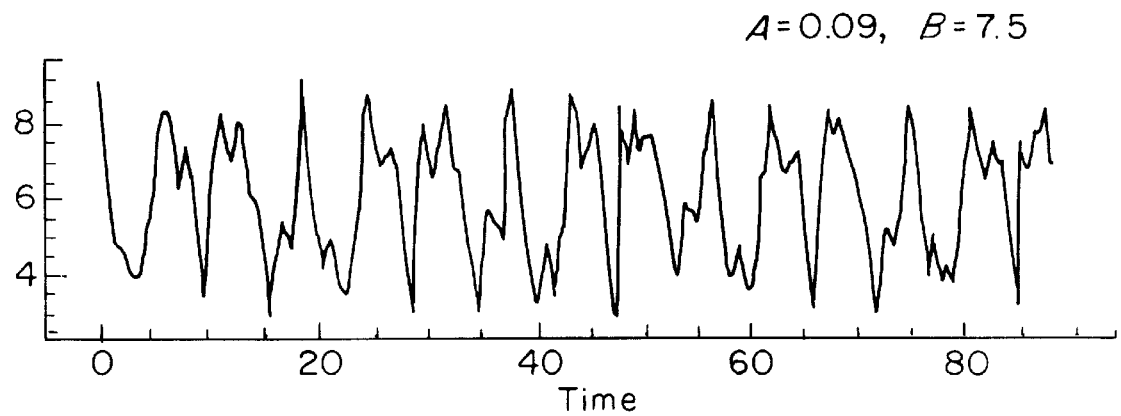
Figure 9A:
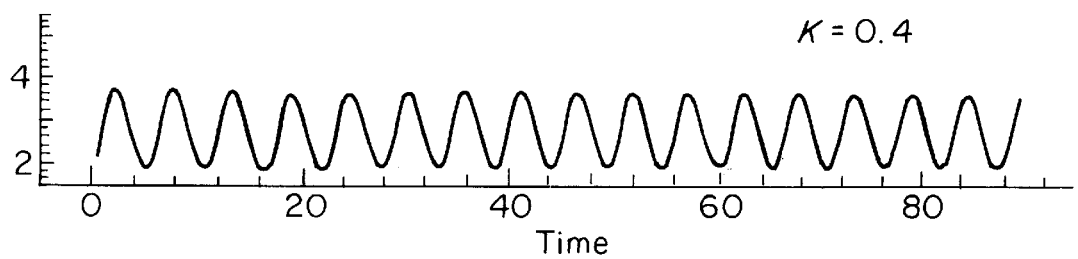
FIGS. 9A–E illustrate luteinizing hormone (LH) time-series output for five coupling parameters in the Rossler coupled differential equation model.
Figure 9B:
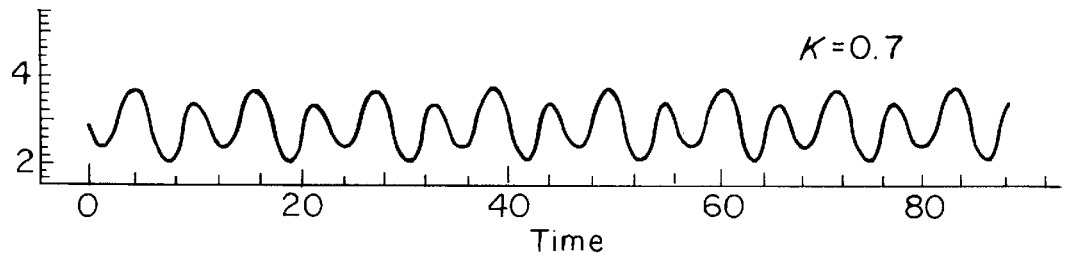
Figure 9C:
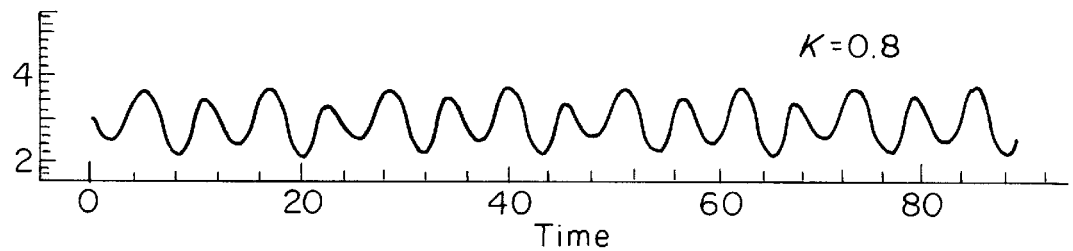
Figure 9D:
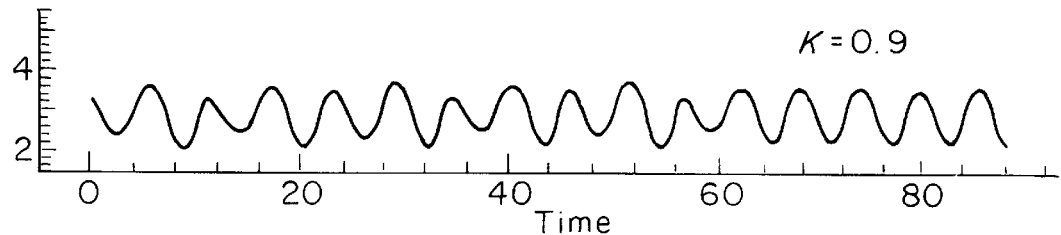
Figure 9E:
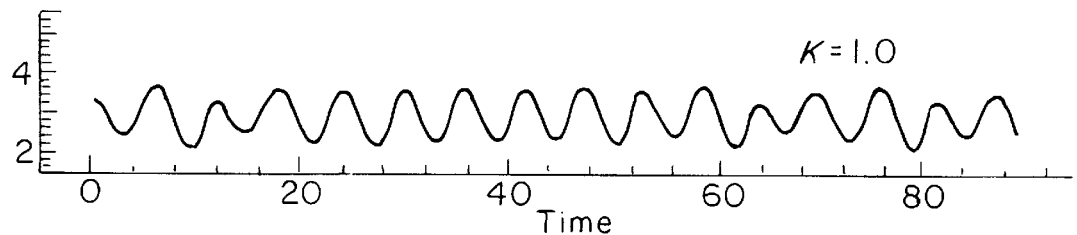

At each noise level ApEn maintains the order of randomness of these versions, although system distinction is much less marked at 0.4 noise level, as shown in FIGS. 8A–C, at which ApEn values are 1.336 for the (0.05, 7.5) case, 1.196 for the (0.05, 8.5) case, and 1.292 for the (0.09, 7.5) case. ULTRA also maintains its order of ranking these versions, with pulse counts of 84, 77, and 92 in the same three cases at 0.4 noise standard deviation. It is not surprising that the distinctions among the versions are muddied at this noise level; some of the small wiggles in the base physiological cases are accentuated, some are eliminated, and some new small wiggles emerge with 0.4 level noise.

From analysis of this model, in the presence of noise, ULTRA tends to smooth out the time-series data, in effect eliminating some small wiggles in the process. In some contexts, that may be desirable, but in instances such as this model, in which numerous small, subordinate pulses are present, ULTRA is discarding physiological information.

Rossler Feedback Model

The Rossler Feedback Model is a coupled system of three variables, represented by three ordinary differential equations. This is considered as a putative model for the male reproductive endocrine system, with variables the pituitary portal concentration of LHRH, and the serum concentrations of luteinizing hormone (LH) and testosterone (T). These concentrations are modelled by a coupled feedback system: the LHRH secretion rate is given as a function of the local concentrations of LH and serum testosterone. The LH secretion rate is given as a function of the concentration of LHRH, plus a rate proportional to its own concentration. The testosterone secretion rate is given as a rate proportional to its own concentration, plus a term proportional to the product of the LHRH and testosterone levels. This feedback system is represented as follows, with K to be specified:

$$\dot{LHRH}=-(LH+T) \ \dot{LH}=LHRH+0.2 \ \dot{LHT}=0.2+K \ (LHRH*\%-5T) \quad (6)$$

For each time, and each value of K, the corresponding concentration levels are calculated by an explicit time step method, $\Delta t=0.005$. A time series is extracted from the solution by sampling every 0.5 t-units. For suitable choices of K, the solutions have many of the qualitative features seen in clinical endocrine data. Here each version is defined by a choice for K. Changes in K can be thought to mirror the intensity of interaction between testosterone and LHRH levels.

This system is analyzed for coupling levels K=0.4, 0.7, 0.8, 0.9, and 1.0. All this is done in a post-transient setting, in which the first 90 t-units are omitted from consideration. The solution time-series is then "postprocessed" as follows, to ensure positive values: convert LHRH to 0.1(LHRH)+3.0, convert LH to 0.1 (LH)+3.0, and T to 0.1(T)+3.0. Add white noise to each baseline value, for each of LHRH, LH, and T to deduce the time-series solution to the coupled system. For each noiseless version, two different lengths of series, 180 points and 900 points are analyzed. For the 900 point series, analyze three different versions of the model, K=0.7, 0.8, and 0.9, each under four different noise levels, noise standard deviations of 0.02, 0.05, 0.1, and 0.2. For K=0.8 and K=1.0, also analyze the series with 2000 points.

This model is similar to one examined by Rossler (Rossler, O. E., "An Equation for Continuous Chaos," *Phys. Lett.* 57A (1976): 397–398) as an example of a system that produced chaotic behavior for certain parameter values of K. It is also thematically similar to models by Smith, which are meant to plausibly model the male endocrine system, and are shown to capture some of the essential physiological dynamics of the true reproductive system. The Rossler model was analyzed, rather than the Smith model, for pedagogic reasons: distinctions among versions are sharper for the Rossler model than for the Smith model, though qualitatively quite similar. In any case, this model was analyzed for some of the reasons given by Smith. Relatively simple versions of this system can explain a number of possible qualitative modes of hormonal dynamics: serum concentrations that are constant in time, periodic in time, or chaotic in time. Most importantly, different behavioral modes can result solely from changes in defining system parameters, or internal interactions among the system subcomponents, and need not be produced by and external, driving force. For example, the onset of puberty, in one version of Smith's model, is seen to be generated simply by an appropriate change in certain system parameters, without an external switch or component entering into the fray.

Furthermore, the Rossler model is substantially different from the Ueda model. In particular, the Rossler model is a function of several variables, and is an explicit feedback system. Thus, it is possible that neither ApEn nor ULTRA may detect changes in the feedback (coupling) rate, as seen by varying K. The model analyzed here was chosen to give either periodic, multiply periodic, or chaotic output for the behavior of LH with time, depending on K. In general, with increasing K, there is increasing system complexity: the LH behavior evolves from periodic to multiply periodic to chaotic.

FIGS. 9A–E illustrate LH time-series output for the five coupling parameters of the Rossler coupled differential equation model, K=0.4, 0.7, 0.8, 0.9, and 1.0 in a noiseless environment. Virtually an identical pulse count is apparent in each of these systems. For K=0.4, the system is strictly periodic, while for K=0.7, the system is "twice-periodic," with a higher pulse always followed by a smaller pulse. The system is "four-times periodic" for K=0.8 (high-low-highest-lowest), and chaotic for K=0.9, and K=1.0. In these last two instances, no pattern of multiple pulses forms a fundamental period of its own.

ULTRA's evaluation of the respective noiseless model versions is considered in runs 1–10 of Table 3. Runs 1–5 and 6–10 are 180 and 900 points long, respectively, with each set of 5 runs arranged in increasing K. Runs 1–5 give either 15 or 16 pulses for each series, and runs 6–10 give between 77 and 82 pulses for each series, indicating little version distinction based on pulse count. For the other statistics there is a distinct difference between the K=0.4 case and the other four versions, all of which produce quite similar values. In runs 7–10, the average frequency ranges from 11.28 to 11.63, the standard deviation of the frequency ranges from 0.636 to 0.650, the average amplitude ranges from 3.50 to 3.56, and the standard deviation of the amplitude ranges from 0.130 to 0.175. Only the last of these statistics, the amplitude standard deviation, shows any spread among the four versions, and even for this statistic, the lowest value is achieved for K=0.9, with both K=0.8 and K=1.0 versions slightly higher. This conflicts with intuition, which suggests that a lowest value for each of these statistics should be for either the least or the most complex system.

TABLE 3

ULTRA Statistics

| Run No | No. of Points | Coupling Parameters K | Input Noise SD | Mean | SD | ApEn | No. of Sign Changes | No. of Pulses | Avg. Freq. | SD Freq. | Avg. Amp | SD Amp |
|---|---|---|---|---|---|---|---|---|---|---|---|---|
| 1 | 180 | 0.4 | 0.0 | 2.774 | 0.692 | 0.165 | 32 | 16 | 10.93 | 0.258 | 3.764 | 0.015 |
| 2 | 180 | 0.7 | 0.0 | 2.871 | 0.529 | 0.266 | 32 | 15 | 11.26 | 0.775 | 3.540 | 0.227 |
| 3 | 180 | 0.8 | 0.0 | 2.882 | 0.499 | 0.442 | 31 | 15 | 11.29 | 0.727 | 3.512 | 0.187 |
| 4 | 180 | 0.9 | 0.0 | 2.902 | 0.476 | 0.472 | 30 | 15 | 11.50 | 0.650 | 3.513 | 0.142 |
| 5 | 180 | 1.0 | 0.0 | 2.918 | 0.453 | 0.489 | 30 | 15 | 11.64 | 0.497 | 3.498 | 0.138 |
| 6 | 900 | 0.4 | 0.0 | 2.772 | 0.689 | 0.165 | 164 | 82 | 10.91 | 0.283 | 3.765 | 0.014 |
| 7 | 900 | 0.7 | 0.0 | 2.872 | 0.527 | 0.262 | 159 | 79 | 11.28 | 0.643 | 3.560 | 0.175 |
| 8 | 900 | 0.8 | 0.0 | 2.887 | 0.495 | 0.431 | 157 | 78 | 11.42 | 0.636 | 3.535 | 0.160 |
| 9 | 900 | 0.9 | 0.0 | 2.897 | 0.475 | 0.495 | 155 | 77 | 11.55 | 0.641 | 3.528 | 0.130 |
| 10 | 900 | 1.0 | 0.0 | 2.910 | 0.454 | 0.510 | 154 | 77 | 11.63 | 0.650 | 3.500 | 0.139 |
| 11 | 900 | 0.7 | 0.02 | 2.872 | 0.529 | 0.323 | 159 | 79 | 11.28 | 0.662 | 3.560 | 0.178 |
| 12 | 900 | 0.7 | 0.05 | 2.872 | 0.532 | 0.633 | 161 | 79 | 11.28 | 0.804 | 3.563 | 0.184 |
| 13 | 900 | 0.7 | 0.2 | 2.874 | 0.571 | 1.453 | 354 | 83 | 10.72 | 2.251 | 3.650 | 0.242 |
| 14 | 900 | 0.7 | 0.1 | 2.873 | 0.540 | 1.112 | 227 | 79 | 11.27 | 1.101 | 3.587 | 0.196 |
| 15 | 900 | 0.8 | 0.02 | 2.887 | 0.495 | 0.503 | 157 | 78 | 11.42 | 0.695 | 3.537 | 0.162 |
| 16 | 900 | 0.8 | 0.05 | 2.888 | 0.497 | 0.761 | 161 | 78 | 11.42 | 0.950 | 3.548 | 0.168 |
| 17 | 900 | 0.8 | 0.2 | 2.890 | 0.535 | 1.544 | 365 | 83 | 10.72 | 2.229 | 3.636 | 0.269 |
| 18 | 900 | 0.8 | 0.1 | 2.888 | 0.505 | 1.167 | 213 | 79 | 11.27 | 1.429 | 3.583 | 0.178 |
| 19 | 900 | 0.9 | 0.02 | 2.897 | 0.474 | 0.565 | 155 | 77 | 11.57 | 0.680 | 3.527 | 0.132 |
| 20 | 900 | 0.9 | 0.05 | 2.898 | 0.475 | 0.822 | 167 | 77 | 11.57 | 0.854 | 3.533 | 0.141 |
| 21 | 900 | 0.9 | 0.2 | 2.900 | 0.505 | 1.503 | 395 | 84 | 10.59 | 2.833 | 3.606 | 0.273 |
| 22 | 900 | 0.9 | 0.1 | 2.898 | 0.478 | 1.187 | 247 | 80 | 11.13 | 1.957 | 3.544 | 0.191 |
| 23 | 2,000 | 0.8 | 0.0 | 2.888 | 0.495 | 0.430 | 349 | 174 | 11.43 | 0.639 | 3.537 | 0.156 |
| 24 | 2,000 | 1.0 | 0.0 | 2.908 | 0.453 | 0.505 | 343 | 171 | 11.62 | 0.652 | 3.498 | 0.143 |

The increase in system complexity with increasing K can be further confirmed by phase-space plots. Phase-space plots serve a similar purpose to Poincare sections, to geometrically capture complexity via an appropriate perspective on the data. In a phase-space plot, the trajectory of LHRH versus LH is plotted so each point represents a single "LHRH-LH" pair of values at a fixed instant. Increased complexity manifests itself in more complicated phase-space portraits, which here is with increasing K. If the motion of the LH-system were singly periodic, the portrait would be a simple closed curve. Multiple periodicity is shown by multiple loops in a closed curve. Chaotic behavior is not represented by closed curves. Fine system structure in these versions is apparent with phase-space portraits produced from much longer time-series input than considered here.

For runs 1–5, in increasing K, ApEn values are 0.165, 0.266, 0.442, 0.472, and 0.489, monotonically increasing with K. For the 900 point runs (6–10), corresponding ApEn values are 0.165, 0.262, 0.431, 0.495, and 0.510, again steadily increasing with K. With these longer runs, distinction is sharper between the K=0.8 case and the K=0.9 and K=1.0 cases. Furthermore, ApEn is (slightly) larger for the K=1.0 case than for the K=0.9 case, establishing system distinction despite the presence of chaos in both instances. In addition, the ApEn values remain nearly constant for run lengths greater than 900 points, as indicated by runs 23 and 24. For K=0.8, no noise, ApEn =0.431 with 900 points, while ApEn=0.430 with 2000 points; for K=1.0, no noise, ApEn=0.510 with 900 points, while ApEn=0.505 with 2000 points. Hence for this model, (i) ApEn distinguishes all the versions from each other; (ii) ApEn, via monotonic increase, directly verifies the growing complexity and increased feedback with increased K; and (iii) establishes points (i) and (ii) with no more than 180 points necessary. Runs 11–22 indicate the effects of noise on the ULTRA and ApEn computations. For each of the three versions K=0.7, K=0.8, and K=0.9, four different noise levels were examined, standard deviations of 0.02, 0.05, 0.1 and 0.2, corresponding to CVs of approximately 1%, 2%, 4%, and 8%, for 900 point time-series. ULTRA maintained its pulse count of roughly 80 total pulses throughout these runs, increasingly slightly with noise level of 0.2 to 83, 83, and 84 pulses for the K=0.7, K=0.8, and K=0.9 cases, respectively. As above, this provided little distinction among these three systems. At 0.02 noise, ApEn maintained increasing order with complexity (0.323 vs. 0.503 vs. 0.565); similarly for the 0.05 and 0.1 noise levels (0.633 vs. 0.761 vs. 0.822, 1.112 vs. 1.167 vs. 1.187). With the 0.1 level noise, the system distinctions were becoming blurred, and with 0.2 noise, the system distinctions were obliterated, especially in the K=0.8 vs. K=0.9 cases (1.453 vs. 1.544 vs. 1.503), in which complexity is slightly reversed (due to "realization" and finite sample size issues). This blurring is evident in phase portraits comparing the K=0.8 and K=0.9 cases at 0.2 noise (data not shown).

Figure 10A:
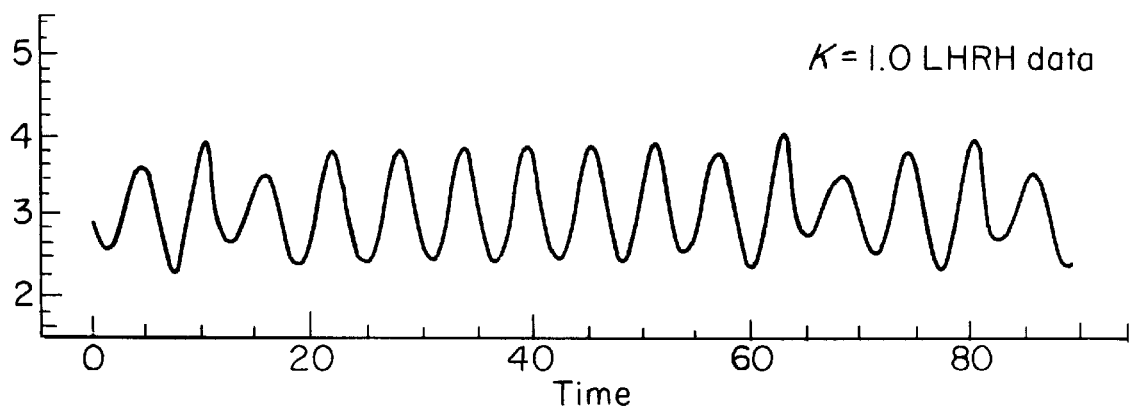
FIGS. 10A–C are Rossler coupled differential equation model time-series output for LHRH data, LH data, and testosterone data.
Figure 10B:
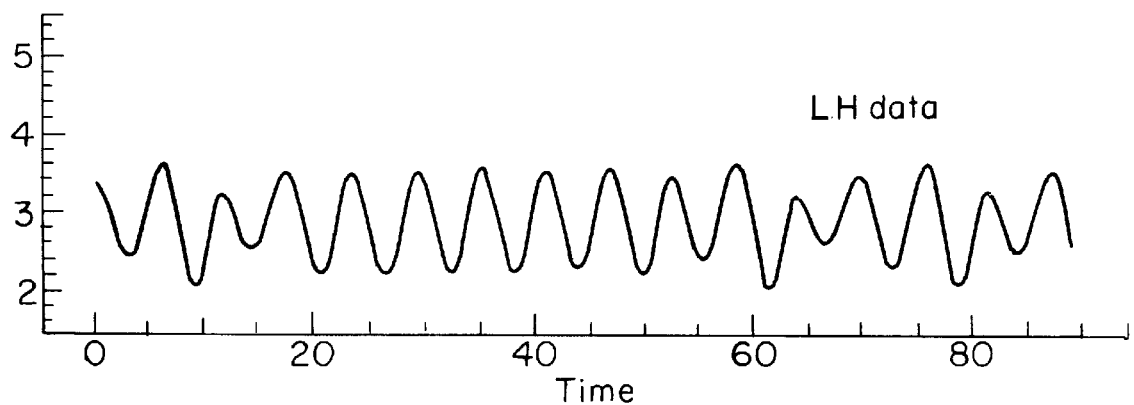
Figure 10C:
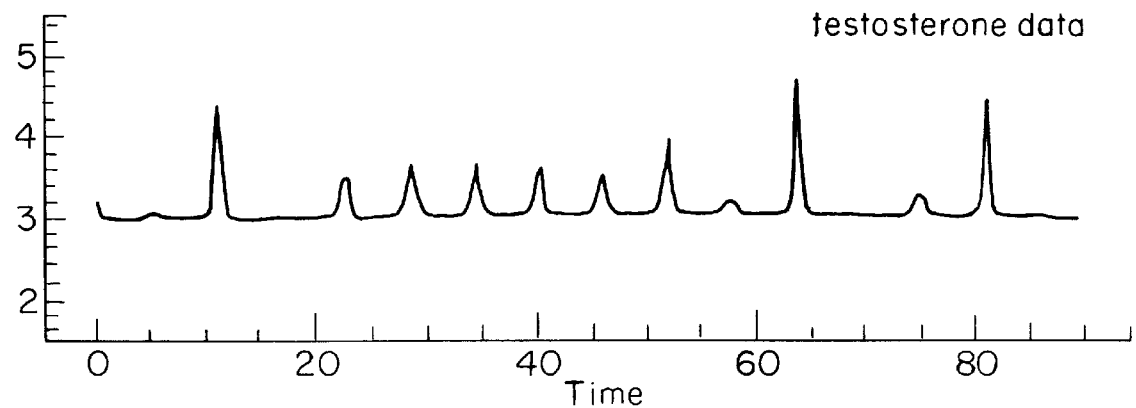

FIGS. 10A—C compares the LHRH, LH, and T time-series from the K=1.0 version of this model, and raises an important issue. The LHRH and LH time-series are visually similar; both have 16 pulses, similar amplitudes and general pulse characteristics. It could be expected that these hormones belong to a single autonomous system. The behavior of T, however, is visually discordant with the behavior of LHRH and LH; there are 12 pulses, long stretches of flat tracings, spiked pulses, and three pulses that are much greater in amplitude than the others. Thus, dissimilar pulsatile characteristics of hormonal plasma concentrations do not eliminate the possibility that the hormones may be derived from a single system, with no external influences.

Discussion and General Conclusions

Some general conclusions from the above runs can be inferred. ApEn and ULTRA provide different and complementary information from the data. ULTRA gives a first-order measure of the pulsatility of the system, via the pulse count and related statistics. ULTRA can be applied to data with 10% CV with 180 data points, typical values for current studies. For some systems, such as those defined by the Ueda and Rossler models above, ULTRA is relatively ineffective at distinguishing distinct versions of the systems, and may possibly give counterintuitive results. Subordinate pulses create difficulties for ULTRA, as do models in which pulse timing is reasonably constant, where the variation is in the patterned versus random behavior of the respective pulse amplitudes. The first-order, as opposed to finely-tuned behavior of ULTRA is further evidenced by the observation that in noiseless systems, ULTRA is statistically equivalent to a sign-change identifying algorithm. This algorithm was noted earlier to be useful, but to lack the greater versatility that appropriately weighted versions maintain.

In contrast, at low intra-assay noise levels, with the stated input parameters ApEn can effectively distinguish all the distinct versions of each model from one another. In directly assessing the regularity of the data, ApEn can distinguish between versions of episodic behavior, as well as between episodic versus more random behavior. By considering all the time-series data, not just the data that make-up the pulse acmes, ApEn evaluates subordinate behavior. There is a significant increase in ApEn with increasing CV, though it is still possible to compare systems with identical intraassay CVs, even as high as 8%, via ApEn to discern system distinction. Such analyses produce ApEn values that are much larger than the corresponding values in noiseless systems; in a few cases, systems that are distinguished by ApEn at low CV are no longer distinguished at 8% CV.

From the Ueda model, it is noted that there may be important regularity information in time-series data that can be effectively extracted only in the presence of a small intra-assay CV. For such purposes, ApEn is well suited, with a finer focus than that of the pulse-detection algorithms currently employed. The required decrease in intraassay CV from current levels is consistent with the direction in which endocrinologists are actively moving. To validate the above claim of effective distinction of model versions by ApEn, an estimate of ApEn standard deviation is determined. The estimate (Monte Carlo estimates, 100 replications per computed standard deviation) is provided for two quite different processes: the MIX(p) model introduced in Pincus (Pincus, S. M., "Approximate Entropy as a Measure of System Complexity," *Proc. Natl. Acad. Sci.* 88 (1991): 2297–2301) and a paradigm for chaos, the parameterized logistic map, $f_a(x)=ax(1-x)$, 3.5<a<4.0. First define MIX(p):fix $0 \leq p \leq 1$. Define $X_j=\sqrt{2} \sin(2\pi j/12)$ for all j, $Y_j$=IID (Independent, Identically Distributed) uniform random variables on $[-\sqrt{3}, \sqrt{3}]$, and $Z_j$=IID random variables, $Z_j=1$ with probability p, $Z_j=0$ with probability 1-p. Then define $MIX(p)_j=(1-Z_j)X_j+Z_jY_j$. This is a family of stochastic processes that samples a sine wave for p=0, is IID uniform for p=1, and intuitively becomes more "random" as p increases. For m=2, r=20% of the process standard deviation, and 900 points, the standard deviation of ApEn (MIX(p)), calculated for each 40 values of p equally spaced between 0 and 1, is less than 0.055 for all p. For 180 points, ApEn (same m and r) standard deviation is less than 0.07 for all p.

For the logistic map, the "randomization" needed to make this deterministic map fit a Monte Carlo scenario is given by different choices for the initial condition. For m=2, r=20% of the process standard deviation, and 900 points, the standard deviation of ApEn ($f_a(x)$), calculated for each of 50 values of "a" equally spaced between 3.5 and 4.0, is less than 0.015 for all a. For 180 points, ApEn (same m and r) standard deviation is less than 0.035 for all a. Thus ApEn values of a=1.1 and b=0.9 would have very high probability of coming from different processes, for either of these two model classes. The MIX process computation is appealing, in that the process is nearly IID (uncorrelated iterates) for p near 1. Because larger ApEn standard deviation generally corresponds to more uncorrelated processes, it is expected that the standard deviation bounds for ApEn for MIX(p) will provide bounds for a large class of deterministic and stochastic processes.

Given the ApEn sensitivity to intra-assay CV, several caveats must be noted to ensure appropriate application of this method. If the same process is analyzed in two different laboratories, one with CV 2%, the other with CV 8%, the ApEn values can be significantly different. Also, if the same process is analyzed under two very different sampling regimens (e.g., samplings every 5 minutes, versus every 20 minutes), ApEn values can be quite different; in effect, the relative noise levels can be dissimilar. Thus, until CVs and other "noise levels" that vary from system to system are markedly reduced from present values, comparison of ApEn values should be restricted to data sets produced from similar settings (e.g., same laboratory and sampling frequency), which would ensure a relatively constant CV across samples. The comparisons done for the two models above, at a fixed CV level, model such a "homogeneously noise" environment, and as already noted, show valid ApEn distinction, given CVs at presently observed levels. Along the same lines, it is critical to distinguish between the comparison of ApEn (with fixed m and r) values for two data sets, given N data points, from the questions of convergence of ApEn for a specific system. The results from the two models analyzed above indicate that ApEn typically needed on the order of 900 points for convergence. In comparing systems with 180 data samples, ApEn distinguished most systems that were distinguished with 900 points, occasionally less sharply. Thus, a fixed sample length should be used for all data sets under study.

The models analyzed above were chosen to illustrate different types of physiologically plausible behavior, and while there was no substantial effort to model a particular endocrine system, it would seem likely that a true endocrine system would be at least as mathematically complex as either of these models. Thus it is imperative that statistics, meant to evaluate pulses generated by true endocrine system hormones, be capable of effective discrimination of versions of the above models. A key observation from these models is that nonlinear systems can produce highly nontrivial, episodic, yet non-periodic output behavior from equations that are simple in appearance. Output that appears as a sequence of identical, sine wave-like pulses is usually associated with uncoupled, linear systems. Such linear systems have been extensively studied because they readily yield exact, analytic mathematical solutions. There is no a priori reason to anticipate that true endocrine systems be either linear or devoid of feedback. Hence, the likelihood that episodicity (no exactly repeating patterns) is physiologically normative must be considered.

In addition to those considered above, stochastic models, such as Markov processes and networks of queues, could have been analyzed. Similar qualitative conclusions to those realized herein are anticipated.

In complex systems of glands and hormones, a direct barometer of feedback, or interaction between systems would likely be insightful. Either a breakdown in or an excessive amount of feedback may mark the onset of disease, and a method that could directly mark such a change in feedback has added value. For the Rossler model, as the coupling parameter K was increased, ApEn steadily increased, thus providing a direct measure of increasing system complexity. In general, ApEn appears to increase with greater system coupling and greater attendant complexity. While coupled systems currently must be individually analyzed to ensure this increase of ApEn with feedback parameter, this property holds significant potential utility in practical applications.

Above, potential near-term applicability was indicated, by observing that with 180 points, or with 8% CV, ApEn still was useful in drawing distinctions between most model versions. In a preferred embodiment of the invention, a randomized version of ApEn is applied to hormone level data. This randomized version of ApEn has the advantage that it can be coupled with bootstrapping methods (Efron, B., *The Jacknife, the Bootstrap, and Other Resampling Plans, Philadelphia*:SIAM, 1982: 27–36) to yield a statistic that distinguishes data sets of 100 points with high probability (via a small variance), in the presence of nontrivial noise. Hence, greater applicability of ApEn to hormone level data can be achieved both by more accurate and numerous clinical data, and by statistical advances outside the clinical setting.

In summary, the potential use of approximate entropoxy (ApEn) to quantify regularity in endocrine hormone data has been described. ApEn offers new insights in the detection of abnormal behavior, especially given modest increases in the number of data samples and in the accuracy of the serum concentration level at each sampling.

Turbulence Measurement and Flow Control

When a fluid impinges on an object, the undisturbed fluid pressure and the velocity of the fluid changes. Depending on the shape of the object, a wake may be formed, which sheds eddies. The eddies may be aperiodic or periodic. The formation of wakes is dependent on the Reynolds number, which is a dimensionless ratio of the inertial force to the viscous force of the fluid.

An object in a fluid stream may be subject to the downstream shedding of vortices from alternating sides of the upstream object. As the wake frequency approaches the natural frequency of the structure, the periodic lift force increases asymptotically in magnitude. When resonance occurs, the structure fails. The neglection of this phenomenon has accounted for failures of numerous structures, including electric transmission lines, smokestacks, and bridges.

Turbulence also affects the amount of fraction or drag between the object and the medium. As the fluid flow transitions from laminar to turbulent, the coefficient of drag increases. Increased drag results in inefficient flow of the medium past the object. The inefficiency caused by turbulence requires that additional energy be exerted to maintain the flow of the medium. For example, a vehicle (or vessel) in motion consumes more fuel when the air flow (or water flow) in the wake is turbulent instead of laminar. Hence, it is desirable to maintain laminar flow as long as possible.

A preferred embodiment of the invention uses a negative feedback system to create maximum or minimum turbulence of a fluid flowing around a primary solid. Classical control or optimum control techniques are used. A secondary solid, smaller than the primary solid is placed in the fluid in such a fashion as to either encourage or discourage turbulence. The turbulence is controlled by critically pulsing, shaping, slowing or otherwise metering the fluid. The system can be adjusted for a small amount of turbulence that minimizes stress on the surface of the primary solid while maximizing flow, or any other complex combination of variables with a desired result.

Figure 11:
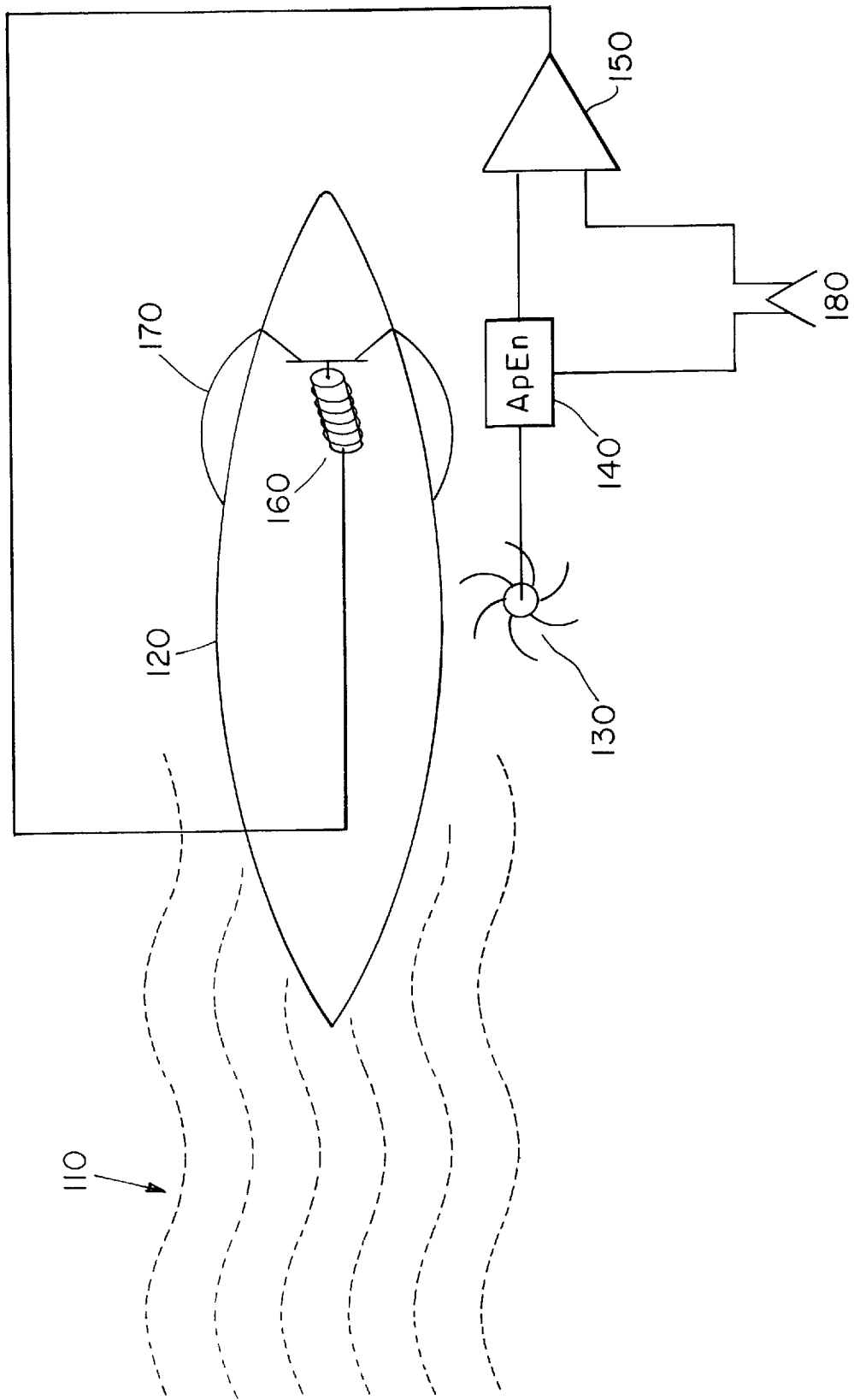
FIG. 11 is a schematic block diagram of a preferred embodiment of a turbulence measurement and flow control device.

FIG. 11 is a schematic block diagram of a preferred embodiment of a turbulence measurement and flow control device according to the present invention. A medium 110, such as a fluid or a gas, is shown flowing across or through a region constrained by a primary solid 120. The medium 110 includes but is not limited to air, water, and blood. The primary solid 120 may be an airfoil or a hydrofoil (e.g. a wing, a propeller blade, or a rudder), a valve, a tube, a pipe, a channel, or any other structure that partially interferes with the flow of the medium 110. In particular, the primary solid 120 may be an artificial heart valve. The flow parameters of the medium 110 are measured by at least one sensor 130. The sensors 130 detect and quantify parameters such as speed, pressure, and direction of flow at specific locations in proximity to the primary solid 120.

The measured parameters from sensors 130 are provided to a computational unit 140, which employs digital computations of approximate entropy to determine a time-varying parameter ApEn(t) for the medium 110 in proximity to the primary solid 120. The ApEn(t) parameter is continuously provided to a compensated negative feedback control 150.

The system uses ApEn as a time-varying measure of turbulence, rather than the classical Reynolds Number, because ApEn is easier to measure, more immune to measurement noise and error, scale length independent, and completely shape independent.

The feedback control 150 generates an optimum time-varying signal to provide to an actuator 160. The actuator 160 moves a secondary solid 170. The secondary solid 170 may be a constrictor, a flap, a vibrating plate, or any other structure that affects the flow of the medium 110, so as to change and optimize the flow characteristics of the medium 110 in proximity to the primary solid 120. In a stagnate medium, the approximate entropy will equal zero. Increasing turbulence is indicated by an increasing value for approximate entropy. The optimum time-varying signal will attempt to either converge ApEn(t)=0 to reduce turbulence or diverge ApEn(t)>0 to increase turbulence.

Auxiliary inputs 180 to the computational unit 140 and to the feedback control 150 provide manual adjustment of desired flow characteristics, so an alternate parameter can be optimized. The alternate parameters may be a combined function of the magnitude of turbulence, the flow speed, and the pressure.

Assessment of DNA Sequences

Approximate entropy (ApEn) can also be directly applied to quantify or associate measures of irregularity of deoxyribonucleic acid (DNA) sequences. DNA is a series of amino acids, which are identified in the DNA sequence using the letters A, C, G and T. The sequence can be very short or very long. Each of these letters can be assigned a different integer value between 1 and 4, inclusive. For example, A=1, C=2, G=3, and T=4. As such, the DNA sequence "AACGGTT-TAAT . . . " can be rewritten as "11233444114 . . .". DNA sequences are typically provided in either man-readable or machine-readable format.

Figure 12:
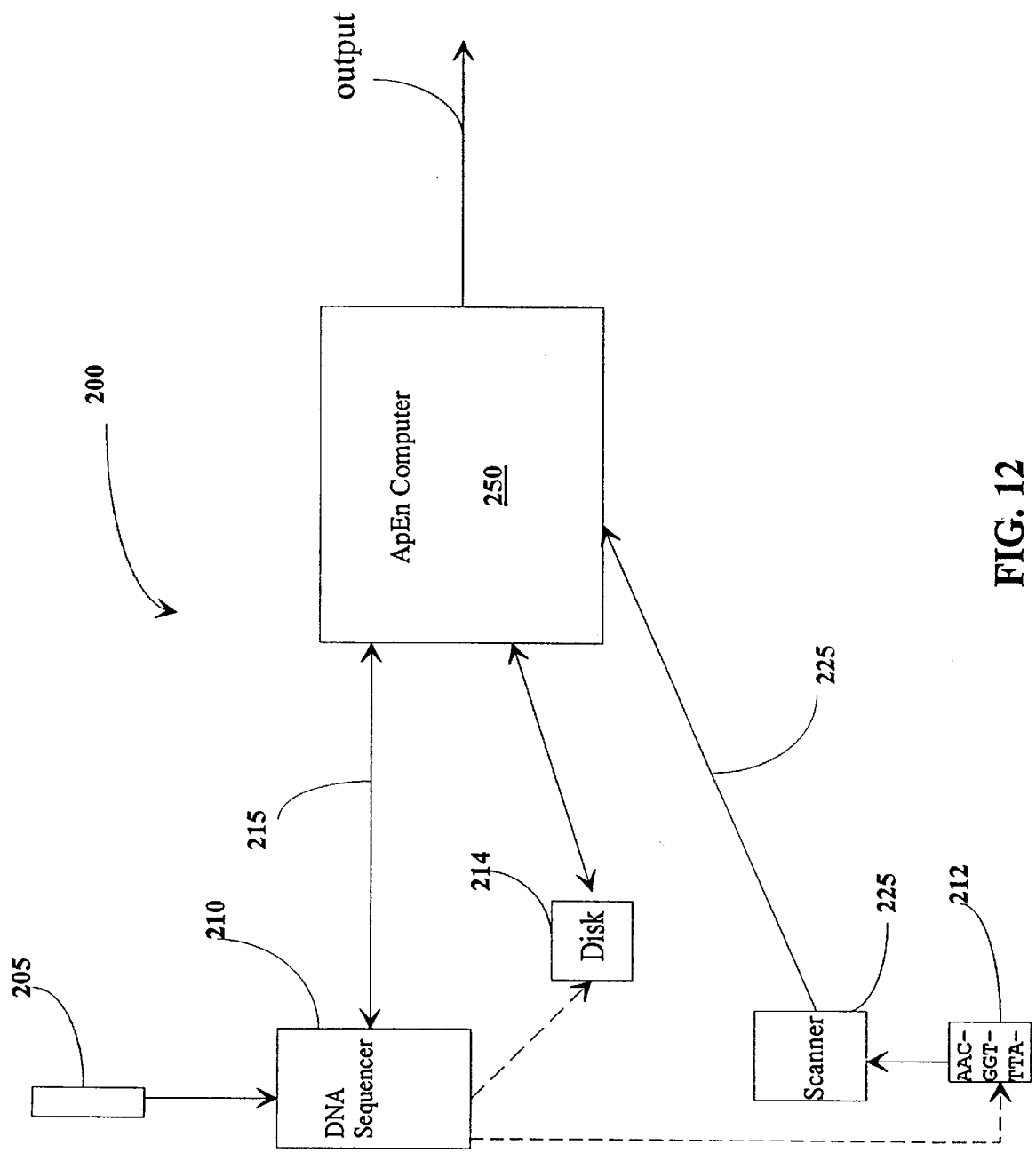
FIG. 12 is a schematic diagram of a computing system for assessing DNA sequences.

FIG. 12 is a schematic diagram of a computing system for assessing DNA sequences. The system 200 includes a DNA sequencer 210 in communication with an ApEn computer 250 over a communication link 215. The ApEn computer 250 can be any specific or general purpose computer for computing approximate entropy from the DNA sequence. Although the ApEn computer 250 is illustrated as being separate from the DNA sequence 210, they can be integrated together. A DNA sample is labelled with radioactive material and a sequencing gel 205 is produced using well-known techniques. The DNA sequencer 210 includes a laser scanner to read the sequencing gel 205 representing the sequence of amino acids in the DNA of the sample. Conventional scans of DNA sequences, however, are prone to error. Consequently, most sequencing gels are manually read and transcribed into a sequence listing.

In a preferred embodiment of the invention, a digital data stream representing the DNA sequence read from the gel 205 is generated by the DNA sequencer 210 and transmitted to the ApEn computer 250 over the communication link 215 for real-time evaluation. Alternatively, a man-readable paper listing 212 or a machine-readable disk 214 having the DNA sequence can be automatically generated by the DNA sequencer 210 or manually produced. The listing 212 or disk 214 facilitates off-line or remote evaluation of the DNA sequence. The paper listing 212 is preferably converted to a machine-readable form by a scanner 220 connected to the ApEn computer by a serial cable 225 or by manual entry of the data. The disk 214 can be read by the ApEn computer 250 using a disk drive.

A value for ApEn can now be calculated by the ApEn computer 250 for any (and all) window lengths m, where r<1 (e.g., r=0.5). Thus the ApEn computer can look for exact subpattern matches of length m, and the persistence, or conversely, lack of repetitiveness of same. Once m increases to above about 3 or 4 in ApEn(m) computations, the sequences that ApEn(m) detects as atypical may not be readily detected by cursory, or even studied human inspection. For example, one or two aberrant length 8 sequences (i.e., m=8) somewhere in a DNA sequence of length 1,000,000 are difficult to catch by manual study.

The application of ApEn to assessing DNA sequences are myriad, including the detection of abnormal sequences which may indicate altered genes. That is, assessing sequential irregularity of and subpatterns within the DNA sequence, the DNA itself can be assessed and acted on as appropriate. In addition, ApEn can be used to verify that DNA has been correctly sequenced by automatically checking the DNA sequence for errors. For example, questionable sections of the sequence can be returned to the DNA sequencer 210 over the communication link 215 where the sequencing gel can be rescanned or manually checked to verify the accuracy of the DNA sequence. By using a feed-back loop, ApEn can be used in a more accurate automated DNA sequencing system, thus reducing or eliminating human labor in DNA sequencing.

Equivalents

While the invention has been particularly shown and described with reference to preferred embodiments thereof, it will be understood by those skilled in the art that various changes in form and details may be made without departing from the spirit and scope of the invention as defined by the appended claims. In particular, the invention can be embodied in hardware, software or firmware.

These and all other equivalents are intended to be encompassed by the following claims.

The invention claimed is:

1. In a data processing system, a method of processing a set of data points to determine a relative amount of patternness of the set of data points, comprising the steps of:

providing a set of data points having values representative of a measured data parameter;

operating on the set of data points with a processor, comprising the operating steps of:

a) defining a class of contiguous runs of prescribed length of the set of data points; and b) assigning quantitative values representing a measurement of the regularity and the stability of similar patterns among the elements of the defined class to determine a relative amount of patternness.

2. The method of claim 1 wherein the quantitative values yield a quantification of approximate entropy of the data points.

3. The method of claim 1 wherein the operating step further comprises filtering the contribution of noise from the quantitative values.

4. The method of claim 1 further comprising the step of converting the data into digital form after performing the defining step.

5. The method of claim 1 wherein the data points are provided by a living biosystem.

6. The method of claim 5 wherein the data points are electrocardiograph (EKG) data.

7. The method of claim 5 wherein the data points are electroencephalograph (EEG) data.

8. The method of claim 5 wherein the data points are hormone secretion data.

9. The method of claim 5 wherein the data points are electro-oculogram (EOG) data.

10. The method of claim 5 wherein the data points are electromyogram (EMG) data.

11. The method of claim 5 wherein the data points are respiratory measurements.

12. The method of claim 1 wherein the set of data comprises less than about 1000 data points.

13. The method of claim 1 wherein the set of data points has a coefficient of variance of less than about 10%.

14. The method of claim 1 wherein the providing step comprising converting measurements of a data parameter into the set of data points.

15. The method of claim 1 wherein the data points are financial data.

16. The method of claim 15 wherein the financial data includes stock market data.

17. The method of claim 16 wherein the stock market data includes data from a market index.

18. The data processing system of claim 17 wherein the financial system includes stock market data.

19. The data processing system of claim 18 wherein the financial system includes data from a market index.

20. The data processing system of claim 18 wherein the financial system includes data from an individual stock.

21. The method of claim 16 wherein the stock market data includes data from an individual stock.

22. The method of claim 15 wherein the financial data includes bond market data.

23. In a data processing system, a method to detect a medical abnormality from a set of medical data, comprising the steps of:
   providing a set of medical data having values representative of measurements of a medical data parameter; and
   operating on the set of medical data with a processor, comprising the operating steps of:
      a) defining a class of contiguous runs of prescribed length of the medical data; and
      b) assigning quantitative values representing a measurement the regularity and the stability of similar patterns among the elements of the defined class to determine a relative amount of patternness.

24. The method of claim 23 further comprising, before the assigning step, the steps of;
   comparing each element of the defined class to a plurality of the elements of the defined class to determine regularity and stability of similar patterns among the elements of the defined class thereby filtering a contribution of noise from the determination of regularity and stability.

25. The method of claim 23 further comprising the steps of:
   computing a single measure of the relative amount of patternness of the set of medical data based on an aggregate of the assigned quantitative values; and
   comparing the single measure of the relative amount of patternness in the set of medical data to a predetermined value of patternness.

26. The method of claim 25 wherein the single measure of patternness is a quantification of approximate entropy.

27. The method of claim 23 wherein there are less than about 1000 data measurements in the set of medical data.

28. The method of claim 23 wherein the medical data parameter is heartbeat data.

29. The method of claim 28 wherein the medical abnormality is fetal distress.

30. The method of claim 28 wherein the medical abnormality is sudden infant death syndrome.

31. The method of claim 28 wherein the medical abnormality is an arrhythmia.

32. The method of claim 23 wherein the medical data parameter is hormone secretion data.

33. The method of claim 23 wherein the set of medical data has a coefficient of variance of less than about 10%.

34. The method of claim 23 wherein the providing step comprises converting measurements of a medical data parameter over a period of time into the set of medical data.

35. A data processing system for operating on a sequence of data comprising:
   a) an assignor for defining a class of contiguous runs of prescribed length of a sequence of data;
   b) a comparator for comparing each element of the defined class to a plurality of the elements of the defined class to determine regularity and stability of similar patterns among the elements of the defined class, and for assigning quantitative values to an extent of regularity and stability of similar patterns among elements of the defined class the comparator reducing effects of noise in the sequence of data from the values that are compared; and
   c) a computation unit for using the quantity measures produced by the comparator to compute an approximate entropy value.

36. The data processing system of claim 35 wherein the sequence of data is measured from a living biosystem over time.

37. The data processing system of claim 35 wherein the sequence of data is measured from a financial system.

38. The data processing system of claim 37 wherein the financial system includes bond market data.

39. An apparatus having a data processor for detecting a medical abnormality from measured medical data parameters comprising:
   an assignor for defining a class of contiguous runs of prescribed length of a sequence of data representing measurements of the medical data parameters over time;
   a comparator for comparing each element of the defined class to a plurality of the elements of the defined class to determine regularity and stability of similar patterns among the elements of the defined class, and for assigning quantitative values to an extent of regularity and stability of similar patterns among elements of the defined class the comparator reducing effects of noise in the sequence of data from the values that are compared; and
   a computation unit for using the quantity measures produced by the comparator to compute an approximate entropy value.

40. In a data processing system, a method of assessing a deoxyribonucleic acid (DNA) sequence comprising the steps of:
   providing a set of data values representative of a DNA sequence;
   operating on the set of data values with a processor, comprising the operating steps of:
      a) defining a class of contiguous runs of prescribed length of the set of data values; and
      b) assigning quantitative values representing a measurement of the regularity and the stability of similar patterns among the elements of the defined class to determine a relative amount of patternness.

41. The method of claim 40 wherein the quantitative values yield a quantification of approximate entropy of the DNA sequence.

42. The method of claim 40 wherein the providing step comprising converting measurements of a labelled gene into the set of data values.

43. The method of claim 40 further comprising the step of detecting a genetic defect from the quantitative values.

44. The method of claim 40 further comprising the step of detecting errors in the DNA sequence from the quantitative values.

45. A data processing system for operating on a deoxyribonucleic acid (DNA) sequence, comprising:
   a) an assignor for defining a class of contiguous runs of prescribed length of a sequence of DNA; and
   b) a computation unit for assigning quantitative values to an extent of regularity and stability of similar patterns among elements of the defined class.

46. The data processing system of claim 45 wherein the computation unit compares each element of the defined class to a plurality of the elements of the defined class to determine regularity and stability of similar patterns among the elements of the defined class.

47. The data processing system of claim 45 wherein the computation unit computes an approximate entropy value from the quantitative values.

48. The data processing system of claim 45 wherein the computational unit detects a genetic defect.

49. The data processing system of claim 45 wherein the computational unit detects errors in the DNA sequence.

* * * * *